(12) United States Patent
Bussolari et al.

(10) Patent No.: US 8,183,213 B2
(45) Date of Patent: May 22, 2012

(54) COMBINATION THERAPY COMPRISING GLUCOSE REABSORPTION INHIBITORS AND RETINOID-X RECEPTOR MODULATORS

(75) Inventors: Jacqueline C. Bussolari, Skillman, NJ (US); Xiaoli Chen, Belle Mead, NJ (US); Bruce R. Conway, Doylestown, PA (US); Keith T. Demarest, Flemington, NJ (US); Hamish N. M. Ross, Far Hills, NJ (US); Rafael Severino, Madrid (ES)

(73) Assignee: Ortho McNeil Pharmaceutical, Inc., Raritan, NJ (US)

( * ) Notice: Subject to any disclaimer, the term of this patent is extended or adjusted under 35 U.S.C. 154(b) by 952 days.

(21) Appl. No.: 11/923,187

(22) Filed: Oct. 24, 2007

(65) Prior Publication Data

US 2009/0075864 A1    Mar. 19, 2009

Related U.S. Application Data

(60) Continuation of application No. 10/372,517, filed on Feb. 24, 2003, now abandoned, which is a division of application No. 10/115,725, filed on Apr. 3, 2002, now Pat. No. 6,838,442.

(60) Provisional application No. 60/281,479, filed on Apr. 4, 2001.

(51) Int. Cl.
  *A61K 31/70*    (2006.01)
  *A61K 31/425*   (2006.01)
  *A61K 31/35*    (2006.01)
  *A61K 31/335*   (2006.01)

(52) U.S. Cl. .......... 514/25; 514/365; 514/369; 514/451; 514/452; 514/866

(58) Field of Classification Search ............... 514/25, 514/365, 369, 451, 452, 866
  See application file for complete search history.

(56) References Cited

U.S. PATENT DOCUMENTS

| | | |
|---|---|---|
| 5,424,406 A | 6/1995 | Tsujihara et al. |
| 5,731,292 A | 3/1998 | Tsujihara et al. |
| 5,731,299 A | 3/1998 | Ebetino et al. |
| 5,767,094 A | 6/1998 | Tsujihara et al. |
| 5,830,873 A | 11/1998 | Tsujihara et al. |
| 6,048,842 A | 4/2000 | Tsujihara et al. |
| 6,130,216 A | 10/2000 | Antonucci et al. |
| 6,153,632 A | 11/2000 | Rieveley |
| 6,515,003 B1 | 2/2003 | Pfahl et al. |
| 6,686,337 B2 | 2/2004 | Connor |
| 6,777,435 B1 | 8/2004 | Momose et al. |
| 7,179,823 B1 | 2/2007 | Momose et al. |
| 7,393,838 B2 | 7/2008 | Fujikura et al. |
| 7,429,568 B2 | 9/2008 | Fujikura et al. |
| 7,465,713 B2 | 12/2008 | Fujikura et al. |
| 7,989,424 B2 | 8/2011 | Fujikura et al. |
| 2008/0096802 A1 | 4/2008 | Bussolari et al. |

FOREIGN PATENT DOCUMENTS

| | | |
|---|---|---|
| EP | 1 213 296 A1 | 6/2002 |
| JP | 124684/97 A | 5/1997 |
| JP | 2000080041 A | 3/2000 |
| WO | WO 97/10819 A | 3/1997 |
| WO | WO 98/57635 A1 | 12/1998 |
| WO | WO 00/61127 A2 | 10/2000 |
| WO | WO 01/16122 A1 | 3/2001 |
| WO | WO 01/16123 | 3/2001 |
| WO | WO 01/17513 A2 | 3/2001 |
| WO | WO 0114372 A2 | 3/2001 |
| WO | WO 01/74834 A | 10/2001 |
| WO | WO 01/74835 A | 10/2001 |
| WO | WO 02/053573 A1 | 7/2002 |
| WO | WO 02/080936 A1 | 10/2002 |

OTHER PUBLICATIONS

Buse, J.B., Gumbiner, B. Mathias, N.P.et al. "Troglitazone use in insulin-treated type 2 diabetic patients"; The Troglitazone insulin study group, Diabetes Care 21: pp. 1455-1461 (1998).

Cha B.S. et al: Peroxisome proliferator-activated receptor (PPAR) gamma and retinoid X receptor (RXR) agonists have complementary effects on glucose and lipid metabolism in human skeletal muscle; Diabetologia, Apr. 2001, pp. 444-452, vol. 44, No. 4, Germany; ISSN: 0012-186X; XP002206000.

Consoli, Agostino, MD. "Role of Liver in Pathophysiology of NIDDM", Diabetes Care, vol. 15, No. 3, Mar. 1992 pp. 430-441.

Day, C. "Thiazolidinediones: a new clas of antidiabetic drugs", Diabetic Medicine, vol. 16, No. 3, 1999, pp. 179-192.

Deetjen, Peter et al. "Renal Handling of D-Glucose and Other Sugars", 1935 pp. 90-94.

Evans, Alison J. and Krentz, Andrew J., "Recent Developments and Emerging Therapies for Type 2 Diabetes Mellitus", Drugs R&D 2:Aug 2, 1999, pp. 75-94.

Freychet, P. , "Pancreatic Hormones". In Hormones from molecules to disease, Kelly. P.A. Baulieu. E.E., eds.. Routledge, Chapman and Hall, New York, NY pp. 491-532.

Gerich, J.E., "Role of Liver and Muscle in Type II Diabetes", Horm. Metab. Res., vol. 26, 1992, pp. 18-21.

Groop, L.C. "Drug treatment on non-insulin-dependent diabetes mellitus" Textbook of Diabetes, Pickup, J.C., Williams. G. eds., Blackwell Science Oxford, UK, 1-18, 1997, pp. 38.1-38.18.

Lee, Wen-Sen et al., "The High Affinity Na+/Glucose Cotransporter", The Journal of Biological Chemistry, vol. 269, No. 16, Apr. 22, 1994, pp. 12032-12039.

Link, J. T. and Sorensen, Bryan K., "A method for preparing c-glycosides related to phlorizin", Tetrahedron Letters 41 , 2000, pp. 9213-9217.

Mackenzie, Bryan et al. "SAAT1 Is a Low Affinity Na +/Glucose Cotransporter and Not an Amino Acid Transporter", The Journal of Biological Chemistry, vol. 269 No. 36, Issue of Sep. 9, 1994, pp. 22488-22491.

Windholz at al., The Merck Index, Tenth Edition (1983) pp. 723 and 724 abstract No. 4866.

(Continued)

*Primary Examiner* — Kevin E Weddington

(57) ABSTRACT

Combination therapy comprising RXR modulators and glucose reabsorption inhibitors useful for the treatment of diabetes and Syndrome X are disclosed.

5 Claims, No Drawings

OTHER PUBLICATIONS

Oku, Akira et al.,"T-1095, an Inhibitor of Renal Na+-Glucose Cotransporters, May Provide a Novel Approach to Treating Diabetes", Diabetes, vol. 48, Sep. 1999, pp. 1794-1800.

Rossetti, Luciano et al., "Correction of Hyperglycermia with Phlorizin Normalizes Tissue Sensitivity to Insulin in Diabetic Rats", J. Clin. Invest., vol. 79, May 1987, pp. 1510-1515.

Rosetti, Luciano et al., "Glucose Toxicity", Diabetes Care, vol. 13, No. 6, Jun. 1990 pp. 610-630.

Silverman, Mel and Turner James, R., "Glucose transport in the renal proximal tubule", Chapter 43, Membrane Biology Group. Dept. of Medicine, University of Toronto, Toronto, Ontario, Canada, , 1992 pp. 2017-2038.

Unger, R.H. and Grundy, S., "Hyperglycaemia as an inducer as well as a consequence of impaired islet cell function and insulin resistance: implications for the management of diabetes", Diabetologia, vol. 28, 1985 pp. 119-121.

You, Guofeng at al., "Molecular Characteristics of Na+-coupled Glucose Transporters in Adult and Embryonic Rat Kidney", The Journal of Biological Chemistry, vol. 270. No. 49, Issue of Dec. 8, 1995, pp. 29365-29371.

Mukherjee, R., Davies, P.J.A., Crombie, D.L., Dischoff, E.D. Cesario, R.M. et al.; "Sensitization of diabetic and obese mice to insulin by retinoid X receptor agonists"; Nature 386: pp. 407-410 (1997).

Nestler, J.E., Jakubowicz, D.J., Reamer, P. et al. "Ovulatory and metabolic effects of D-chiro-inositol in the polycystic ovary syndrome"; N. Engl. J. Med. 340: pp. 1314-1320 (1999).

Schwartz, S., Raskin, P., Fonseca, V., and Graveline, J.F. "Effect of troglitazone in insulin-treated patients with type 2 diabetes"; N. Engl. J. Med, 338: pp. 861-866 (1998).

Knowler WC et al, Preventing Non-Insulin-Dependent Diabetes. Diabetes, 1995, 44: 483-488.

UK Prospective Diabetes Study Group, "Effect of intensive blood gluose control with metformin on complications in overweight patients with type 2 diabetes", Lancet 352: pp. 854-865, (1998).

UK Prospective Diabetes Study Group, "Intensive blood-glucose control with sulfphonylureas or insulin compared with conventional treatment and risk of complications inpatients with type 2 diatetes"; Lancet 352: pp. 837-853 (1998).

US 8,183,213 B2

COMBINATION THERAPY COMPRISING GLUCOSE REABSORPTION INHIBITORS AND RETINOID-X RECEPTOR MODULATORS

CROSS REFERENCE TO RELATED APPLICATIONS

This application is a continuation of U.S. application Ser. No. 10/372,517, filed on Feb. 24, 2003, now abandoned which is a divisional of U.S. application Ser. No. 10/115,725, filed on Apr. 3, 2002, now issued as U.S. Pat. No. 6,838,442, which claims priority from the provisional application U.S. Ser. No. 60/281,479 filed on Apr. 4, 2001, which applications are incorporated herein by reference.

FIELD OF THE INVENTION

This invention relates to a novel method and compositions for the treatment or prophylaxis of diabetes and Syndrome X.

BACKGROUND OF THE INVENTION

Diabetes is a chronic disorder affecting carbohydrate, fat and protein metabolism in animals.

Type I diabetes mellitus, which comprises approximately 10% of all diabetes cases, was previously referred to as insulin-dependent diabetes mellitus ("IDDM") or juvenile-onset diabetes. This disease is characterized by a progressive loss of insulin secretory function by beta cells of the pancreas. This characteristic is also shared by non-idiopathic, or "secondary", diabetes having its origins in pancreatic disease. Type I diabetes mellitus is associated with the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Type II diabetes mellitus (non-insulin-dependent diabetes mellitus or NIDDM) is a metabolic disorder involving the dysregulation of glucose metabolism and impaired insulin sensitivity. Type II diabetes mellitus usually develops in adulthood and is associated with the body's inability to utilize or make sufficient insulin. In addition to the insulin resistance observed in the target tissues, patients suffering from type II diabetes mellitus have a relative insulin deficiency—that is, patients have lower than predicted insulin levels for a given plasma glucose concentration. Type II diabetes mellitus is characterized by the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Syndrome X, also termed Insulin Resistance Syndrome (IRS), Metabolic Syndrome, or Metabolic Syndrome X, is recognized in some 2% of diagnostic coronary catheterizations. Often disabling, it presents symptoms or risk factors for the development of Type II diabetes mellitus and cardiovascular disease, including impaired glucose tolerance (IGT), impaired fasting glucose (IFG), hyperinsulinemia, insulin resistance, dyslipidemia (e.g., high triglycerides, low HDL), hypertension and obesity.

Therapy for IDDM patients has consistently focused on administration of exogenous insulin, which may be derived from various sources (e.g., human, bovine, porcine insulin). The use of heterologous species material gives rise to formation of anti-insulin antibodies which have activity-limiting effects and result in progressive requirements for larger doses in order to achieve desired hypoglycemic effects.

Typical treatment of Type II diabetes mellitus focuses on maintaining the blood glucose level as near to normal as possible with lifestyle modification relating to diet and exercise, and when necessary, the treatment with anti-diabetic agents, insulin or a combination thereof. NIDDM that cannot be controlled by dietary management is treated with oral antidiabetic agents.

Although insulin resistance is not always treated in all Syndrome X patients, those who exhibit a prediabetic state (e.g., IGT, IFG), where fasting glucose levels may be higher than normal but not at the diabetes diagnostic criterion, is treated in some countries (e.g., Germany) with metformin to prevent diabetes. The anti-diabetic agents may be combined with pharmacological agents for the treatment of the concomitant co-morbidities (e.g., antihypertensives for hypertension, hypolipidemic agents for lipidemia).

First-line therapies typically include metformin and sulfonylureas as well as thiazolidinediones. Metformin monotherapy is a first line choice, particularly for treating type II diabetic patients who are also obese and/or dyslipidemic. Lack of an appropriate response to metformin is often followed by treatment with metformin in combination with sulfonylureas, thiazolidinediones, or insulin. Sulfonylurea monotherapy (including all generations of drugs) is also a common first line treatment option. Another first line therapy choice may be thiazolidinediones. Alpha glucosidase inhibitors are also used as first and second line therapies. Patients who do not respond appropriately to oral anti-diabetic monotherapy, are given combinations of the above-mentioned agents. When glycemic control cannot be maintained with oral antidiabetics alone, insulin therapy is used either as a monotherapy, or in combination with oral antidiabetic agents.

One recent development in treating hyperglycemia is focused on excretion of excessive glucose directly into urine. Specific inhibitors of SGLTs have been shown to increase the excretion of glucose in urine and lower blood glucose levels in rodent models of IDDM and NIDDM. However, combination therapy comprising a retinoid-X receptor (RXR) modulator and a glucose reabsorption inhibitor has not been contemplated in the art.

SUMMARY OF THE INVENTION

The present invention is directed to methods and compositions for the treatment or prophylaxis of diabetes, Syndrome X, or associated symptoms or complications. More specifically, this invention is directed to a novel method of treating diabetes or Syndrome X, or associated symptoms or complications thereof, in a subject afflicted with such a condition, said method comprising administering one or more glucose reabsorption inhibitors and administering one or more RXR modulators for the treatment of diabetes or Syndrome X, or associated symptoms or complications thereof.

One aspect of the invention features a pharmaceutical composition comprising a glucose reabsorption inhibitor, an RXR modulator, and a pharmaceutically acceptable carrier. The invention also provides a process for formulating a pharmaceutical composition, comprising formulating together a glucose reabsorption inhibitor, an RXR modulator, and a pharmaceutically acceptable carrier.

An embodiment of the invention is a method for treating diabetes or Syndrome X, or associated symptoms or complications thereof in a subject, said method comprising administering to said subject a jointly effective amount of a glucose reabsorption inhibitor and administering to said subject a jointly effective amount of an RXR modulator, said combined administration providing the desired therapeutic effect.

Another embodiment of the invention is a method for inhibiting the onset of diabetes or Syndrome X, or associated symptoms or complications thereof in a subject, said method comprising administering to said subject a jointly effective dose of a glucose reabsorption inhibitor and administering to said subject a jointly effective amount of an RXR modulator, said combined administration providing the desired prophylactic effect.

In the disclosed methods, the diabetes or Syndrome X, or associated symptoms or complications thereof, is selected from IDDM, NIDDM, IGT, IFG, obesity, nephropathy, neuropathy, retinopathy, atherosclerosis, polycystic ovary syndrome or polycystic ovarian syndrome, hypertension, ischemia, stroke, heart disease, irritable bowel disorder, inflammation, and cataracts.

Also included in the invention is the use of one or more glucose reabsorption inhibitors in combination with one or more RXR modulators for the preparation of a medicament for treating a condition selected from IDDM, NIDDM, IGT, IFG, obesity, nephropathy, neuropathy, retinopathy, atherosclerosis, polycystic ovary syndrome or polycystic ovarian syndrome, hypertension, ischemia, stroke, heart disease, irritable bowel disorder, inflammation, and cataracts.

DETAILED DESCRIPTION OF THE INVENTION

All diabetics, regardless of their genetic and environmental backgrounds, have in common an apparent lack of insulin or inadequate insulin function. Because transfer of glucose from the blood into muscle and fatty tissue is insulin dependent, diabetics lack the ability to utilize glucose adequately, which leads to undesired accumulation of glucose in the blood (hyperglycemia). Chronic hyperglycemia leads to decrease in insulin secretion and contributes to increased insulin resistance, and as a result, the blood glucose concentration is increased so that diabetes is self-exacerbated (Diabetologia, 1985, "Hyperglycaemia as an inducer as well as a consequence of impaired isle cell function and insulin resistance: implications for the management of diabetes", Vol. 28, p. 119); Diabetes Cares, 1990, Vol. 13, No. 6, "Glucose Toxicity", pp. 610-630). Therefore, by treating hyperglycemia, the aforementioned self-exacerbating cycle is interrupted so that the prophylaxis or treatment of diabetes is made possible.

U.S. Pat. No. 6,153,632 to R. Rieveley discloses a method and composition stated to be for the treatment of diabetes mellitus (Type I, Impaired Glucose Tolerance ["IGT"] and Type II), which incorporates a therapeutic amount of one or more insulin sensitizers along with one or more of an orally ingested insulin, an injected insulin, a sulfonylurea, a biguanide or an alpha-glucosidase inhibitor for the treatment of diabetes mellitus.

According to one aspect, the invention features the combination of a PPAR modulator, preferably a PPAR δ agonist, and an SGLT inhibitor, preferably an SGLT 2 inhibitor or a selective SGLT 2 inhibitor.

A. Terms

Some terms are defined below and by their usage throughout this disclosure.

Unless otherwise noted, "alkyl" and "alkoxy" as used herein, whether used alone or as part of a substituent group, include straight, cyclic, and branched-chain alkyl having 1 to 8 carbon atoms, or any number within this range. For example, alkyl radicals include methyl, ethyl, n-propyl, isopropyl, n-butyl, isobutyl, sec-butyl, t-butyl, 2-butenyl, 2-butynyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. The alkyl and alkoxy group may be independently substituted with one to five, preferably one to three groups selected from halogen (F, Cl, Br, I), oxo, OH, amino, carboxyl, and alkoxy. The alkyl and alkoxy group may also be independently linked to one or more PEG radicals (polyethylene glycol).

The term "acyl" as used herein, whether used alone or as part of a substituent group, means an organic radical having 2 to 6 carbon atoms (branched or straight chain) derived from an organic acid by removal of the hydroxyl group. The acyl group is, for example, an optionally substituted $C_{2-20}$ alkanoyl group, a lower alkoxy-lower alkanoyl group, an optionally substituted lower alkoxycarbonyl group, an optionally substituted benzoyl group, an optionally substituted phenoxycarbonyl group, or an amino acid residue which is obtained by removing a hydroxy group from the carboxyl group of a corresponding amino acid (wherein amino groups and/or carboxyl groups in said residue may be protected by a conventional protecting group). The term "Ac" as used herein, whether used alone or as part of a substituent group, means acetyl.

"Aryl" is a carbocyclic aromatic radical including, but not limited to, phenyl, 1- or 2-naphthyl and the like. The carbocyclic aromatic radical may be substituted by independent replacement of 1 to 3 of the hydrogen atoms thereon with halogen, OH, CN, mercapto, nitro, amino, cyano, optionally substituted $C_1$-$C_8$-alkyl, optionally substituted alkoxy, alkylthio, alkylsulfinyl, alkylsulfonyl, alkyl-amino, di($C_1$-$C_8$-alkyl)amino, formyl, carboxyl, alkoxycarbonyl, alkoxycarbonyloxy, alkanoyloxy, phenyl, carbamoyl, carboxamide, di-lower alkylcarbamoyloxy, phenoxycarbonyloxy group, lower alkylenedioxy, benzoyloxy, alkyl-CO—O—, alkyl-O—CO—, —CONH$_2$, alkyl-O—CO—O—, or alkyl-CO—NH—Illustrative aryl radicals include, for example, phenyl, naphthyl, biphenyl, indene

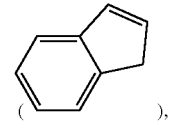

( ), indane

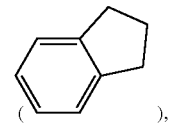

( ), fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl.

The term "heteroaryl" as used herein represents a stable five or six-membered monocyclic or bicyclic aromatic ring system which consists of carbon atoms and from one to three heteroatoms selected from N, O and S. The heteroaryl group may be attached at any heteroatom or carbon atom, which results in the creation of a stable structure. Examples of heteroaryl groups include, but are not limited to benzofuranyl, benzothiophenyl, pyridinyl, pyrazinyl, pyridazinyl, pyrimidinyl, thiophenyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl or quinolinyl. Preferred heteroaryl groups include pyridinyl, thiophenyl, furanyl, and quinolinyl. When the heteroaryl group is substituted, the heteroaryl group may have one to three substituents which are independently selected from halogen, OH, CN, mercapto, nitro, amino, cyano, optionally substituted $C_1$-$C_8$-alkyl, optionally substituted alkoxy, alkylthio, alkylsulfinyl, alkylsulfonyl, alkyl-amino, di($C_1$-$C_8$-alkyl)amino, formyl, carboxyl, alkoxycarbonyl, alkoxycarbonyloxy, alkanoyloxy, phenyl, carbamoyl, carboxamide, di-lower alkylcarbamoyloxy, phenoxycarbonyloxy group, lower alkylenedioxy, benzoyloxy, alkyl-CO—O—, alkyl-O—CO—, —$CONH_2$, alkyl-O—CO—O—, or alkyl-CO—NH—.

The terms "heterocycle," "heterocyclic," and "heterocyclyl" refer to an optionally substituted, fully or partially saturated cyclic group which is, for example, a 4- to 7-membered monocyclic, 7- to 11-membered bicyclic, or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom.

Exemplary monocyclic heterocyclic groups include pyrrolidinyl; oxetanyl; pyrazolinyl; imidazolinyl; imidazolidinyl; oxazolyl; oxazolidinyl; isoxazolinyl; thiazolidinyl; isothiazolidinyl; tetrahydrofuryl; piperidinyl; piperazinyl; 2-oxopiperazinyl; 2-oxopiperidinyl; 2-oxopyrrolidinyl; 4-piperidonyl; tetrahydropyranyl; tetrahydrothiopyranyl; tetrahydrothiopyranyl sulfone; morpholinyl; thiomorpholinyl; thiomorpholinyl sulfoxide; thiomorpholinyl sulfone; 1,3-dioxolane; dioxanyl; thietanyl; thiiranyl; and the like. Exemplary bicyclic heterocyclic groups include quinuclidinyl; tetrahydroisoquinolinyl; dihydroisoindolyl; dihydroquinazolinyl (such as 3,4-dihydro-4-oxo-quinazolinyl); dihydrobenzofuryl; dihydrobenzothienyl; dihydrobenzothiopyranyl; dihydrobenzothiopyranyl sulfone; dihydrobenzopyranyl; indolinyl; isochromanyl; isoindolinyl; piperonyl; tetrahydroquinolinyl; and the like. When the heteroaryl group is substituted, the heterocyclyl may be independently substituted with one to five, preferably one to three groups selected from halogen, OH, CN, mercapto, nitro, amino, cyano, optionally substituted $C_1$-$C_8$-alkyl, optionally substituted alkoxy, alkylthio, alkylsulfinyl, alkylsulfonyl, alkyl-amino, di($C_1$-$C_8$-alkyl) amino, formyl, carboxyl, alkoxycarbonyl, alkoxycarbonyloxy, alkanoyloxy, phenyl, carbamoyl, carboxamide, di-lower alkylcarbamoyloxy, phenoxycarbonyloxy group, lower alkylenedioxy, benzoyloxy, alkyl-CO—O—, alkyl-O—CO—, —$CONH_2$, alkyl-O—CO—O—, or alkyl-CO—NH—.

The term "composition" is intended to encompass a product comprising the specified ingredients in the specified amounts, as well as any product which results, directly or indirectly, from combinations of the specified ingredients in the specified amounts.

The term "combined administration" includes co-administration wherein: 1) the two or more agents are administered to a subject at substantially similar times; and 2) the two or more agents are administered to a subject at different times, at independent intervals which may or may not overlap or coincide.

The term "subject" as used herein, refers to an animal, preferably a mammal, most preferably a human, who is the object of treatment, observation or experiment.

The term "RXR modulator" as used herein, refers to Retinoid-X receptor agonists, partial agonists, or antagonists. Preferably the modulator increases insulin sensitivity. According to one aspect, the modulator is an RXR agonist.

Diabetes, Syndrome X, and associated symptoms or complications include such conditions as IDDM, NIDDM, IGT, IFG, obesity, nephropathy, neuropathy, retinopathy, atherosclerosis, polycystic ovary syndrome, polycystic ovarian syndrome, hypertension, ischemia, stroke, heart disease, irritable bowel disorder, inflammation, and cataracts. Examples of a prediabetic state includes IGT and IFG.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician, the delaying of which disorder is mediated by the modulation of glucose reabsorption activity or RXR activity or both. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together.

The term "protecting groups" refer to those moieties known in the art that are used to mask functional groups; protecting groups may be removed during subsequent synthetic transformations or by metabolic or other in vivo administration conditions. During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known in the art. Examples of hydroxyl and diol protecting groups are provided below.

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, and polyethyleneglycol ethers.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate), and polyethyleneglycol esters.

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate, and polyethyleneglycol carbonates.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate(tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

Protection for 1,2- and 1,3-Diols

Cyclic Acetals and Ketals

Examples of cyclic acetals and ketals include methylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Silyl Derivatives

Examples of silyl derivatives include di-t-butylsilylene group, and 1,3-(1,1,3,3-tetraisopropyldisiloxanylidene) derivative.

B. Glucose Reabsorption Inhibitors

One method of treating hyperglycemia is to excrete excessive glucose directly into urine so that the blood glucose concentration is normalized. For example, sodium-glucose cotransporters (SGLTs), primarily found in chorionic membrane of the intestine and the kidney, are a family of proteins actively involved in the normal process of glucose absorption. Among them, SGLT1 is present in intestinal and renal epithelial cells (Lee et al., 1994), whereas SGLT2 is found in the epithelium of the kidney (You et al., 1995, MacKenzie et al., 1994). Glucose absorption in the intestine is primarily mediated by SGLT1, a high-affinity low-capacity transporter with a $Na^+$:glucose transport ratio of 2:1. SGLT2, also known as SAAT1, transports $Na^+$ and glucose at a ratio of 1:1 and functions as a low-affinity high-capacity transporter. These SGLTs are characterized in Table 1:

TABLE 1

| ISOFORM | TISSUE | Stoichiometry | Preferred Substrate | $K_m$* in vitro | TmG** in vitro | $K_m$* In vivo |
|---|---|---|---|---|---|---|
| SGLT1 | Sm. Intestine | 2:1 | D-glucose D-galactose | 0.1 | nd | Nd |
|  | Kidney (S1, S3) | 2:1 | D-glucose D-galactose | 0.39 | 7.9 | 0.3 |
| SGLT2 (SAAT1) | Kidney (S3) | 1:1 | D-glucose | 1.64 | 83 | 6 |

* (mM) for D-glucose
** Maximal transport rate pmol/min/mm

Renal reabsorption of glucose is mediated by SGLT1 and SGLT2 (Silverman et al., 1992; Deetjen et al., 1995). Plasma glucose is filtered in the glomerulus and is transepithelially reabsorbed in the proximal tubules. SGLT1 and SGLT2 are located in the apical plasma membranes of the epithelium and derive their energy from the inward sodium gradient created by the $Na^+/K^+$ ATPase pumps located on the basolateral membrane. Once reabsorbed, the elevated cytosolic glucose is then transported to the interstitial space by facilitated glucose transports (GLUT1 and GLUT2). Therefore, inhibition of SGLTs reduces plasma glucose through suppression of glucose reabsorption in the kidney. A therapeutically or prophylactically effective amount of an SGLT inhibitor, such as that sufficient to increase urine glucose excretion, or to decrease plasma glucose, in a subject by a desired amount per day, can be readily determined using methods established in the art. Recently, it has been found that phlorizin, a natural glycoside present in barks and stems of Rosaceae (e.g., apple, pear, etc.), inhibits $Na^+$-glucose co-transporters located in chorionic membrane of the intestine and the kidney. By inhibiting $Na^+$-glucose co-transporter activity, phlorizin inhibits the renal tubular glucose reabsorption and promotes the excretion of glucose so that the glucose level in a plasma is controlled at a normal level for a long time via subcutaneous daily administration (Journal of Clinical Investigation, 1987, Vol. 79, p. 1510).

JP 8-347406, filed Dec. 26, 1996, and U.S. Pat. Nos. 5,767,094, 5,830,873, and 6,048,842 (all to Tanabe Seiyaku Co., Ltd.) disclose propiophenone derivatives having hypoglycemic activity by inhibiting sodium-glucose cotransporter activity. JP2762903, JP2795162, JP2906978, and U.S. Pat. Nos. 5,424,406 and 5,731,292, all to Tanabe Seiyaku Co., Ltd., disclose dihydrochalcone derivatives having hypoglycemic activity based on the urine glucose increasing activity thereof.

In particular, U.S. Pat. No. 6,048,842 discloses a compound, or a pharmaceutically acceptable salt thereof, useful for treatment and/or prophylaxis of diabetes, which has the structure of Formula I:

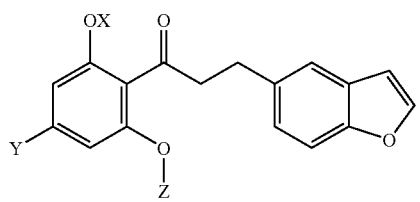

(I)

wherein OX is a hydroxy group which may optionally be protected, Y is a lower alkyl group, and Z is a β-D-glucopyranosyl group wherein one or more hydroxy groups may optionally be protected.

Where OX of Formula I is a protected hydroxy group, the protecting group may be any protecting group which can be a protecting group for a phenolic hydroxy group, for example, a lower alkoxy-lower alkyl group such as methoxymethyl group; an allyl group; and an acyl group such as a lower alkanoyl group, a lower alkoxy-lower alkanoyl group, a lower alkoxycarbonyl group, a lower alkoxy-lower alkoxycarbonyl group, an arylcarbonyl group (e.g., benzoyl group). Among these protecting groups, preferable ones are an acyl group such as a lower alkanoyl group, a lower alkoxy-lower alkanoyl group, a lower alkoxycarbonyl group, a lower alkoxy-lower alkoxycarbonyl group, and especially preferable ones are a lower alkanoyl group, and a lower alkoxycarbonyl group.

Where Z of Formula I is a β-D-glucopyranosyl group wherein one or more hydroxy groups are protected, the protecting group may be any conventional protecting groups for hydroxy group which can easily be removed by a conventional method such as acid-treatment, hydrolysis, reduction, etc. The β-D-glucopyranosyl group wherein one or more hydroxy groups are protected by the above-mentioned protecting groups may be selected from (i) a β-D-glucopyranosyl group wherein one or more hydroxy groups are acylated, (ii) a β-D-glucopyranosyl group wherein two hydroxy groups combine to form a 1-lower alkoxy-lower alkylidenedioxy group, a benzylidenedioxy group, a phosphinicodioxy group, or a carbonyldioxy group together with the protecting groups thereof, and (iii) a β-D-glucopyranosyl group wherein one or two hydroxy groups are acylated, and the other two hydroxy groups combine to form a 1-lower alkoxy-lower alkylidenedioxy group, a benzylidenedioxy group, a phosphinicodioxy group, or a carbonyldioxy group together with the protecting groups thereof. However, the protecting groups for the hydroxy groups of the β-D-glucopyranosyl group should not be construed to be limited to the above protecting groups, and may be any ones which can be removed after administering the present compound into the living body and give the hydroxy groups of the β-D-glucopyranosyl group, or can promote the absorption of the desired compound into the living body, or make it more easy to administer the present compound into the living body, or can increase the solubility in oil and/or water of the present compound.

When the hydroxy group of the β-D-glucopyranosyl group is acylated, the acyl group is preferably a lower alkanoyl group, a lower alkoxy-lower alkanoyl group, a lower alkoxycarbonyl group, a lower alkoxy-lower alkoxycarbonyl group, or an arylcarbonyl group (e.g., benzoyl group), or an amino acid residue which is obtained by removing a hydroxy group from the carboxyl group of a corresponding amino acid (wherein amino groups and/or carboxyl groups and/or hydroxy groups in said residue may be protected by a conventional protecting group). The amino acid residue includes a group which is obtained by removing a hydroxy group from the carboxyl group of a natural amino acid such as aspartic acid, glutamic acid, glutamine, serine, sarcosine, proline, phenylalanine, leucine, isoleucine, glycine, tryptophan, cysteine, histidine, tyrosine, or valine, or an antipode thereof, or a racemic compound thereof.

When Z is a β-D-glucopyranosyl group wherein two hydroxy groups of the β-D-glucopyranosyl group combine to form a 1-lower alkoxy-lower alkylidenedioxy group, a benzylidenedioxy group, a phosphinicodioxy group, or a carbonyldioxy group together with the protecting groups thereof, said β-D-glucopyranosyl group may be a β-D-glucopyranosyl group wherein the 4- and 6-hydroxy groups of the β-D-glucopyranosyl group combine to form a 1-lower alkoxy-lower alkylidenedioxy group, a benzylidenedioxy group, a phosphinicodioxy group, or a carbonyldioxy group together with the protecting groups thereof. Such β-D-glucopyranosyl group has one of the following two formulae:

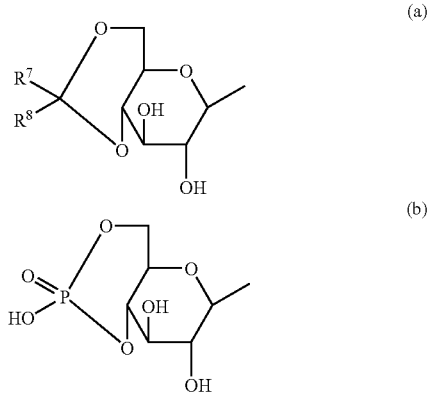

wherein one of $R^7$ and $R^8$ is a hydrogen atom or a lower alkyl group, and the other is a lower alkoxy group, or one of $R^7$ and $R^8$ is a hydrogen atom, and the other is a phenyl group, or $R^7$ and $R^8$ combine to form an oxo group.

When two hydroxy groups of the β-D-glucopyranosyl group combine to form a 1-lower alkoxy-lower alkylidenedioxy group together with the protecting groups thereof, the 1-lower alkoxy-lower alkylidenedioxy group is preferably a 1-lower alkoxyethylidenedioxy group, and more preferably a 1-methoxyethylidenedioxy group or a 1-ethoxyethylidenedioxy group.

Y of Formula I is preferably an alkyl group having 1 to 4 carbon atoms, more preferably a methyl group or an ethyl group.

The propiophenone derivatives of Formula I or a pharmaceutically acceptable salt thereof include an intramolecular salt thereof, or a solvate or hydrate thereof, as well.

In addition, U.S. Pat. No. 5,830,873 discloses a compound, or a pharmaceutically acceptable salt thereof, useful for treatment and/or prophylaxis of diabetes which has the structure of Formula II:

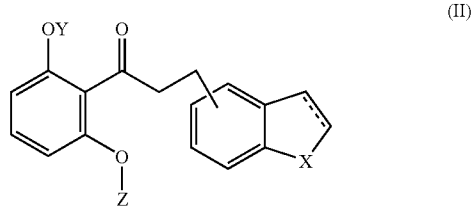

wherein X is an oxygen atom, a sulfur atom or a methylene group, OY is a protected or unprotected hydroxy group, Z is a β-D-glucopyranosyl group or 4-O-(α-D-glucopyranosyl)-β-D-glucopyranosyl group wherein one or more hydroxy groups of these groups may optionally be acylated, and the dotted line means the presence or absence of a double bond.

Furthermore, U.S. Pat. No. 5,767,094 discloses a compound, or a pharmaceutically acceptable salt thereof, useful for treatment and/or prophylaxis of diabetes which has the structure of Formula III:

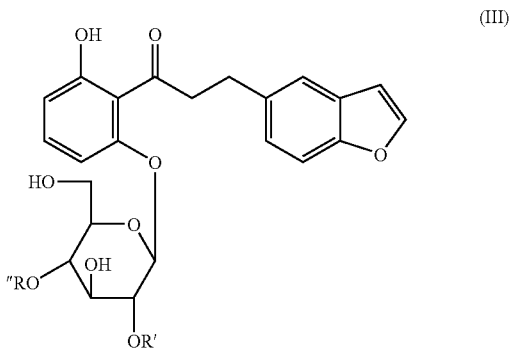

wherein R' is a lower alkanoyl group, and R" is a hydrogen atom, or R' is a hydrogen atom, and R" is a lower alkoxycarbonyl group.

Furthermore, U.S. Pat. Nos. 5,424,406 and 5,731,292 disclose a compound, or a pharmaceutically acceptable salt thereof, useful for treatment and/or prophylaxis of diabetes which has the structure of Formula IV:

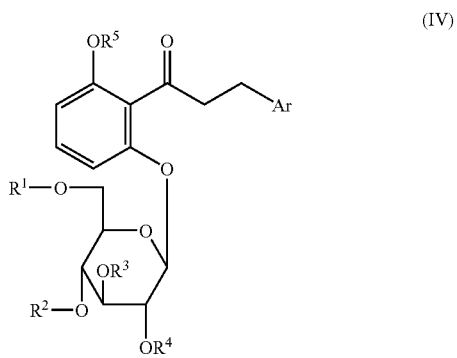

wherein Ar is an aryl group, $R^1$ is hydrogen atom or an acyl group, $R^2$ is hydrogen atom, an acyl group or α-D-glucopyranosyl group, or $R^1$ and $R^2$ may combine together to form a substituted methylene group, $R^3$ and $R^4$ are each hydrogen atom or an acyl group, and $OR^5$ is a protected or unprotected hydroxy group or a lower alkoxy group.

Other SGLT inhibitors include alkyl- and phenyl-glucosides, 1-5-isoquinolinesulfonyl)-2-methylpiperazine-HCl (indirectly via protein kinase C), p-chloromercuribenzoate (PCMB), N,N'-dicyclohexylcarbodiimide (DCCD), copper and cadmium ions, and trivalent lanthanides.

The compounds of formulae I, II, III, IV, and V may be prepared by the processes disclosed in U.S. Pat. Nos. 5,424,406, 5,731,292, 5,767,094, 5,830,873, and 6,048,842.

C. RXR Modulators

Retinoid-X receptor (RXR) modulators are also insulin sensitizing drugs, which include, but are not limited to:

(1) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455);

(2) 9-cis-retinoic acid;

(3) AGN-4326 (also known as ALRT-4204, AGN-4204, ALRT-326, ALRT-324, or LGD 1324);

(4) LGD 1324 (ALRT 324);

(5) LG 100754;

(6) LY-510929;

(7) LGD 1268 (6-(1,1,4,4,6-pentamethyl-1,2,3,4-tetrahydro-naphth-7-ylcycloprop-1-yl)nicotinic acid, known as ALRT 268 or LG 100268);

(8) LG 100264; and (9) substituted heterocycles such as compounds of Formula VI,

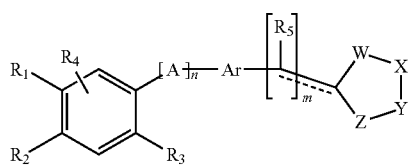

VI wherein n and m are independently 0 or 1;

$R_1$ and $R_2$ are 1) independently or together hydrogen, alkyl, substituted alkyl, haloalkyl, alkenyl, substituted alkenyl, alkynyl, substituted alkynyl, alkoxy, substituted alkoxy, hydroxyl, acyl, amino, mono-substituted amino, di-substituted amino, carboxy, carboalkoxy, alkylcarboxamide, substituted alkylcarboxamide, dialkylcarboxamide, substituted dialkylcarboxamide or haloalkoxy; or 2) $R_1$ and $R_2$ together with the aromatic ring bonded thereto form a cycloalkyl, substituted cycloalkyl, cycloalkenyl, substituted cycloalkenyl residue that may optionally comprise 1 or 2 heteroatoms selected from O, S, NH or N-alkyl;

$R_3$ and $R_4$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, thiohaloalkoxy; carboxy, carboalkoxy, alkylcarboxamide, substituted alkylcarboxamide, dialkylcarboxamide, substituted dialkylcarboxamide;

A is —$CR_6R_7$— wherein $R_6$ and $R_7$ are independently or together hydrogen, alkyl, substituted alkyl, alkoxy, substituted alkoxy, haloalkoxy; or $R_6$ and $R_7$ together form a cycloalkyl residue that may optionally comprise 1 or 2 heteroatoms selected from O, S, NH or N-alkyl;

Ar is Formula VII, VII, IX or X:

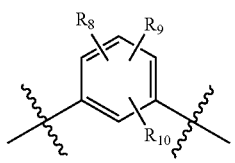

VII

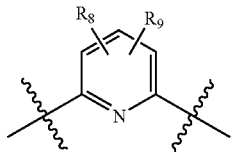

VIII

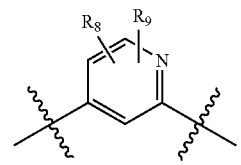

IX

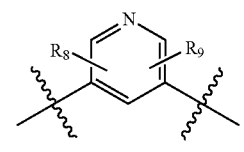

X wherein $R_8$, $R_9$ and $R_{10}$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylamide, alkylsulfonamide, arylsulfonamide, alkylurea, arylurea, alkylcarbamate, arylcarbamate, alkoxy, substituted alkoxy, haloalkoxy, thioalkyl, thiohaloalkoxy; carboxy, carboalkoxy, alkylcarboxamide, substituted alkylcarboxamide, dialkylcarboxamide, substituted dialkylcarboxamide;

$R_5$ is hydrogen, halogen, hydroxy, alkyl or substituted alkyl;

---- represents a bond present or absent; and

W, X, Y and Z are independently or together —C(O)—, —C(S)—, —S—, —O—, or —NH— residues.

One preferred example of compounds of Formula VI is MX-6054, which is 2,4-thiazolidinedione, 5-[[3-(5,6,7,8-tetrahydro-3,5,5,8,8-pentamethyl-2-naphthalenyl)-4-(trifluoromethoxy)phenyl]methylene]-, (5Z)-, also named 3-(3,5,5, 8,8-pentamethyl-5,6,7,8-tetrahydro-2-naphthyl)-4-trifluoromethoxybenzylidene-2,4-thiazolidinedione, represented by the following formula:

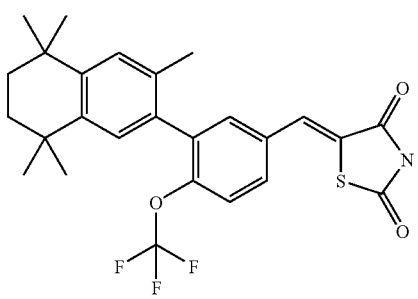

Other preferred examples of RXR modulators include compounds of Formula VI wherein the group

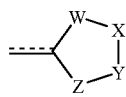

is 2,4-thiazolidinedione

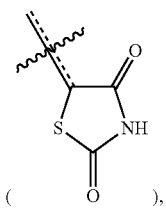

2-thioxo-4-thiazolidinedione

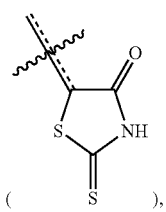

isoxazolidinedione

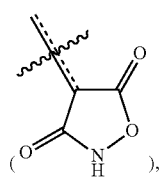

2,4-imidazolidinedione

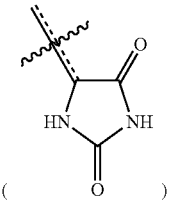

or 2,4-thioxo-4-imidazolidinedione

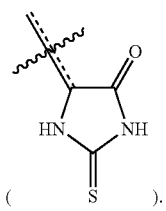

When n is 1, preferably $R_1$ and $R_2$ together with the aromatic ring bonded thereto form a substituted cycloalkyl optionally comprising 1 or 2 heteroatoms selected from O, S, NH or N-alkyl, and $R_3$ is alkyl or substituted alkyl. Also preferably, A is —$CR_6R_7$— wherein $R_6$ and $R_7$ are independently or together alkyl; or $R_6$ and $R_7$ together form a cycloalkyl comprising 1 or 2 oxygen atoms and more preferably a 1,3-dioxolane ring. Still preferably, the group

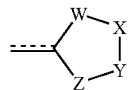

is 2,4-thiazolidinedione, 2-thioxo-4-thiazolidinedione, isoxazolidinedione, 2,4-imidazolidinedione or 2,4-thioxo-4-imidazolidinedione.

Preferably, compounds of Formula VI are selected from:
3-(3,5,5,8,8-pentamethyl-5,6,7,8-tetrahydro-2-naphthyl)-4-trifluoromethoxybenzylidene-2,4-thiazolidinedione;
4-[2-(3,5,5,8,8-pentamethyl-5,6,7,8-tetrahydro-2-naphthyl)-1,3-dioxolane]benzylidene-2,4-thiazolidinedione;
4-[2-(5,5,8,8-tetramethyl-5,6,7,8-tetrahydro-2-naphthyl)-2-propyl]benzylidene-2,4-thiazolidinedione;
4-[2-(3,5,5,8,8-pentamethyl-5,6,7,8-tetrahydro-2-naphthyl)-1,3-dioxolane]benzylidene-2-thioxo-2,4-thiazolidinedione;
4-[2-(5,5,8,8-tetramethyl-5,6,7,8-tetrahydro-2-naphthyl)-2-propyl]benzylidene-2-thioxo-2,4-thiazolidinedione;
4-[2-(3,5,5,8,8-pentamethyl-5,6,7,8-tetrahydro-2-naphthyl)-1,3-dioxolane]benzylidene-2-thioxo-2,4-imidazolidinedione,
4-[2-(5,5,8,8-tetramethyl-5,6,7,8-tetrahydro-2-naphthyl)-2-propyl]benzylidene-2-thioxo-2,4-imidazolidinedione;
4-[2-(3,5,5,8,8-pentamethyl-5,6,7,8-tetrahydro-2-naphthyl)-1,3-dioxolane]benzylidene-2,4-imidazolidinedione;
4-[2-(5,5,8,8-tetramethyl-5,6,7,8-tetrahydro-2-naphthyl)-2-propyl]benzylidene-2,4-imidazolidinedione;
4-[2-(3,5,5,8,8-pentamethyl-5,6,7,8-tetrahydro-2-naphthyl)-1,3-dioxolane]benzyl-2,4-thiazolidinedione;
4-[2-(5,5,8,8-tetramethyl-5,6,7,8-tetrahydro-2-naphthyl)-2-propyl]benzyl-2,4-thiazolidinedione;
4-[2-(3,5,5,8,8-pentamethyl-5,6,7,8-tetrahydro-2-naphthyl)-1,3-dioxolane]benzyl-2-thioxo-2,4-thiazolidinedione;
4-[2-(5,5,8,8-tetramethyl-5,6,7,8-tetrahydro-2-naphthyl)-2-propyl]benzyl-2-thioxo-2,4-thiazolidinedione;
4-[2-(3,5,5,8,8-pentamethyl-5,6,7,8-tetrahydro-2-naphthyl)-1,3-dioxolane]benzyl-2-thioxo-2,4-imidazolidinedione;
4-[2-(5,5,8,8-tetramethyl-5,6,7,8-tetrahydro-2-naphthyl)-2-propyl]benzyl-2-thioxo-2,4-imidazolidinedione;
4-[2-(3,5,5,8,8-pentamethyl-5,6,7,8-tetrahydro-2-naphthyl)-1,3-dioxolane]benzyl-2,4-imidazolidinedione; and
4-[2-(5,5,8,8-tetramethyl-5,6,7,8-tetrahydro-2-naphthyl)-2-propyl]benzyl-2,4-imidazolidinedione.

These and other RXR modulators are disclosed in WO 0116122 and WO 0116123, to Maxia Pharmaceuticals, Inc. These publications also describe materials of making and using the disclosed RXR modulators and are incorporated herein by reference.

D. Additional Antidiabetic Agents

Antidiabetic agents that can be used as a third antidiabetic agent according to the invention include, but are not limited to:

(A) Thiazolidinediones and non-thiazolidinediones insulin sensitizers, which decrease peripheral insulin resistance by enhancing the effects of insulin at target organs and tissues.

Some of these drugs are known to bind and activate the nuclear receptor peroxisome proliferator-activated receptor-gamma (PPARγ) which increases transcription of specific insulin-responsive genes. Examples of PPAR-gamma agonists are thiazolidinediones such as:
(1) rosiglitazone (2,4-thiazolidinedione,5-((4-(2-(methyl-2-pyridinylamino)ethoxy)phenyl)methyl)-, (Z)-2-butenedioate (1:1) or 5-((4-(2-(methyl-2-pyridinylamino)ethoxy)phenyl)methyl)-2,4-thiazolidinedione, known as AVANDIA; also known as BRL 49653, BRL 49653C, BRL 49653c, SB 210232, or rosiglitazone maleate);
(2) pioglitazone (2,4-thiazolidinedione, 5-((4-(2-(5-ethyl-2-pyridinyl)ethoxy)phenyl)methyl)-, monohydrochloride, (+−)- or 5-((4-(2-(5-ethyl-2-pyridyl)ethoxy)phenyl)methy)-2,4-thiazolidinedione, known as ACTOS, ZACTOS, or GLUSTIN; also known as AD 4833, U 72107, U 72107A, U 72107E, pioglitazone hydrochloride (USAN));
(3) troglitazone (5-((4-((3,4-dihydro-6-hydroxy-2,5,7,8-tetramethyl-2H-1-benzopyran-2-yl)methoxy)phenyl)methyl)-2,4-thiazolidinedione, known as NOSCAL, REZULIN, ROMOZIN, or PRELAY; also known as CI 991, CS 045, GR 92132, GR 92132X);
(4) isaglitazone ((+)-5-[[6-[(2-fluorophenyl)methoxy]-2-naphthalenyl]methyl]-2,4-thiazolidinedione or 5-((6-((2-fluorophenyl)methoxy)-2-naphthalenyl)methyl-2,4-thiazolidinedione or 5-(6-(2-fluorobenzyloxy) naphthalen-2-ylmethyl)thiazolidine-2,4-dione, also known as MCC-555 or neoglitazone); and
(5) 5-BTZD.

Additionally, the non-thiazolidinediones that act as insulin sensitizing agents include, but are not limited to:
(1) JT-501 (JTT 501, PNU-1827, PNU-716-MET-0096, or PNU 182716: isoxazolidine-3,5-dione, 4-((4-(2-phenyl-5-methyl)-1,3-oxazolyl)ethylphenyl-4)methyl-);
(2) KRP-297 (5-(2,4-dioxothiazolidin-5-ylmethyl)-2-methoxy-N-(4-(trifluoromethyl)benzyl)benzamide or 5-((2,4-dioxo-5-thiazolidinyl)methyl)-2-methoxy-N-((4-(trifluoromethyl)phenyl)methyl)benzamide); and
(3) Farglitazar (L-tyrosine, N-(2-benzoylphenyl)-o-(2-(5-methyl-2-phenyl-4-oxazolyl)ethyl)- or N-(2-benzoylphenyl)-O-(2-(5-methyl-2-phenyl-4-oxazolyl) ethyl)-L-tyrosine, or GW2570 or GI-262570).

Other agents have also been shown to have PPAR modulator activity such as PPARγ, SPPARγ, and/or PPARα/δ agonist activity. Examples are listed below:
(1) AD 5075;
(2) R 119702 ((+−)-5-(4-(5-Methoxy-1H-benzimidazol-2-ylmethoxy)benzyl)thiazolin-2,4-dione hydrochloride, or CI 1037 or CS 011);
(3) CLX-0940 (peroxisome proliferator-activated receptor alpha agonist/peroxisome proliferator-activated receptor gamma agonist);
(4) LR-90 (2,5,5-tris(4-chlorophenyl)-1,3-dioxane-2-carboxylic acid, PPAR α/γ agonist);
(5) Tularik (PPAR γ agonist);
(6) CLX-0921 (PPAR γ agonist);
(7) CGP-52608 (PPAR agonist);
(8) GW-409890 (PPAR agonist);
(9) GW-7845 (PPAR agonist);
(10) L-764406 (PPAR agonist);
(11) LG-101280 (PPAR agonist);
(12) LM-4156 (PPAR agonist);
(13) Risarestat (CT-112);
(14) YM 440 (PPAR agonist);
(15) AR-H049020 (PPAR agonist);
(16) GW 0072 (4-(4-((2S,5S)-5-(2-(bis(phenylmethyl) amino)-2-oxoethyl)-2-heptyl-4-oxo-3-thiazolidinyl) butyl)benzoic acid);
(17) GW 409544 (GW-544 or GW-409544);
(18) NN 2344 (DRF 2593);
(19) NN 622 (DRF 2725);
(20) AR-H039242 (AZ-242);
(21) GW 9820 (fibrate);
(22) GW 1929 (N-(2-benzoylphenyl)-O-(2-(methyl-2-pyridinylamino)ethyl)-L-tyrosine, known as GW 2331, PPAR α/γ agonist);
(23) SB 219994 ((S)-4-(2-(2-benzoxazolylmethylamino) ethoxy)-alpha-(2,2,2-trifluoroethoxy)benzenepropanoic acid or 3-(4-1-(2-(N-(2-benzoxazolyl)-N-methylamino)ethoxy)phenyl)-2 (S)-(2,2,2-trifluoroethoxy)propionic acid or benzenepropanoic acid,4-(2-(2-benzoxazolylmethylamino)ethoxy)-alpha-(2,2,2-trifluoroethoxy)-, (alphaS)-, PPAR α/γ agonist);
(24) L-796449 (PPAR α/γ agonist);
(25) Fenofibrate (Propanoic acid, 2-[4-(4-chlorobenzoyl) phenoxy]-2-methyl-, 1-methylethyl ester, known as TRICOR, LIPCOR, LIPANTIL, LIPIDIL MICRO PPAR α agonist);
(26) GW-9578 (PPAR α agonist);
(27) GW-2433 (PPAR α/γ agonist);
(28) GW-0207 (PPAR γ agonist);
(29) LG-100641 (PPAR γ agonist);
(30) LY-300512 (PPAR γ agonist);
(31) NID525-209 (NID-525);
(32) VDO-52 (VDO-52);
(33) LG 100754 (peroxisome proliferator-activated receptor agonist);
(34) LY-510929 (peroxisome proliferator-activated receptor agonist);
(35) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455); and
(36) GW-1536 (PPAR α/γ agonist).

(B) Other insulin sensitizing agents include, but are not limited to:
(1) INS-1 (D-chiro inositol or D-1,2,3,4,5,6-hexahydroxycyclohexane);
(2) protein tyrosine phosphatase 1 B (PTP-1B) inhibitors;
(3) glycogen synthase kinase-3 (GSK3) inhibitors;
(4) beta 3 adrenoceptor agonists such as ZD 2079 ((R)-N-(2-(4-(carboxymethyl)phenoxy)ethyl)-N-(2-hydroxy-2-phenethyl) ammonium chloride, also known as ICI D 2079) or AZ 40140;
(5) glycogen phosphorylase inhibitors;
(6) fructose-1,6-bisphosphatase inhibitors;
(7) chromic picolinate, vanadyl sulfate (vanadium oxysulfate);
(8) KP 102 (organo-vanadium compound);
(9) chromic polynicotinate;
(10) potassium channel agonist NN 414;
(11) YM 268 (5,5'-methylene-bis(1,4-phenylene)bismethylenebis (thiazolidine-2,4-dione);
(12) TS 971;
(13) T 174 ((+−)-5-(2,4-dioxothiazolidin-5-ylmethyl)-2-(2-naphthylmethyl)benzoxazole);
(14) SDZ PGU 693 ((+)-trans-2 (S-((4-chlorophenoxy) methyl)-7alpha-(3,4-dichlorophenyl)tetrahydropyrrolo (2,1-b) oxazol-5(6H)-one);
(15) S 15261 ((−)-4-(2-((9H-fluoren-9-ylacetyl)amino) ethyl)benzoic acid 2-((2-methoxy-2-(3-(trifluoromethyl)phenyl)ethyl)amino) ethyl ester);
(16) AZM 134 (Alizyme);
(17) ARIAD;

(18) R 102380;
(19) PNU 140975 (1-(hydrazinoiminomethyl) hydrazino) acetic acid;
(20) PNU 106817 (2-(hydrazinoiminomethyl)hydrazino) acetic acid;
(21) NC 2100 (5-((7-(phenylmethoxy)-3-quinolinyl)methyl)-2,4-thiazolidinedione;
(22) MXC 3255;
(23) MBX 102;
(24) ALT 4037;
(25) AM 454;
(26) JTP 20993 (2-(4-(2-(5-methyl-2-phenyl-4-oxazolyl) ethoxy)benzyl)-malonic acid dimethyl diester);
(27) Dexlipotam (5(R)-(1,2-dithiolan-3-yl)pentanoic acid, also known as (R)-alpha lipoic acid or (R)-thioctic acid);
(28) BM 170744 (2,2-Dichloro-12-(p-chlorophenyl)dodecanoic acid);
(29) BM 152054 (5-(4-(2-(5-methyl-2-(2-thienyl)oxazol-4-yl)ethoxy)benzothien-7-ylmethyl)thiazolidine-2,4-dione);
(30) BM 131258 (5-(4-(2-(5-methyl-2-phenyloxazol-4-yl)ethoxy)benzothien-7-ylmethyl)thiazolidine-2,4-dione);
(31) CRE 16336 (EML 16336);
(32) HQL 975 (3-(4-(2-(5-methyl-2-phenyloxazol-4-yl) ethoxy)phenyl)-2 (S)-(propylamino) propionic acid);
(33) DRF 2189 (5-((4-(2-(1-Indolyl)ethoxy)phenyl)methyl) thiazolidine-2,4-dione);
(34) DRF 554158;
(35) DRF-NPCC;
(36) CLX 0100, CLX 0101, CLX 0900, or CLX 0901;
(37) IkappaB Kinase (IKK B) Inhibitors
(38) mitogen-activated protein kinase (MAPK) inhibitors p38 MAPK Stimulators
(39) phosphatidyl-inositide triphosphate
(40) insulin recycling receptor inhibitors
(41) glucose transporter 4 modulators
(42) TNF-α antagonists
(43) plasma cell differentiation antigen-1 (PC-1) Antagonists
(44) adipocyte lipid-binding protein (ALBP/aP2) inhibitors
(45) phosphoglycans
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V-411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (G FAT) modulators.

(C) Biguanides, which decrease liver glucose production and increases the uptake of glucose. Examples include metformin such as:
(1) 1,1-dimethylbiguanide (e.g., Metformin—DepoMed, Metformin—Biovail Corporation, or METFORMIN GR (metformin gastric retention polymer)); and
(2) metformin hydrochloride (N,N-dimethylimidodicarbonimidic diamide monohydrochloride, also known as LA 6023, BMS 207150, GLUCOPHAGE, or GLUCOPHAGE XR.

(D) Alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the post-prandial glucose peak. Examples include, but are not limited to:
(1) acarbose (D-glucose, O-4,6-dideoxy-4-(((1S-(1alpha, 4alpha,5beta,6alpha))-4,5,6-trihydroxy-3-(hydroxymethyl)-2-cyclohexen-1-yl)amino)-alpha-D-glucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUMIDA, or ASCAROSE);
(2) Miglitol (3,4,5-piperidinetriol, 1-(2-hydroxyethyl)-2-(hydroxymethyl)-, (2R(2alpha, 3beta, 4alpha, 5beta))- or (2R,3R,4R,5S)-1-(2-hydroxyethyl)-2-(hydroxymethyl-3,4,5-piperidinetriol, also known as BAY 1099, BAY M 1099, BAY-m-1099, BAYGLITOL, DIASTABOL, GLYSET, MIGLIBAY, MITOLBAY, PLUMAROL);
(3) CKD-711 (0-4-deoxy-4-((2,3-epoxy-3-hydroxymethyl-4,5,6-trihydroxycyclohexane-1-yl)amino)-alpha-b-glucopyranosyl-(1-4)-alpha-D-glucopyranosyl-(1-4)-D-glucopyranose);
(4) emiglitate (4-(2-((2R,3R,4R,5S)-3,4,5-trihydroxy-2-(hydroxymethyl)-1-piperidinyl)ethoxy)benzoic acid ethyl ester, also known as BAY o 1248 or MKC 542);
(5) MOR 14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and
(6) Voglibose (3,4-dideoxy-4-((2-hydroxy-1-(hydroxymethyl)ethyl)amino)-2-C-(hydroxymethyl)-D-epi-inositol or D-epi-Inositol,3,4-dideoxy-4-((2-hydroxy-1-(hydroxymethyl)ethyl)amino)-2-C-(hydroxymethyl)-, also known as A 71100, AO 128, BASEN, GLUSTAT, VOGLISTAT.

(E) Insulins include regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to
(1) Biota;
(2) LP 100;
(3) (SP-5-21)-oxobis(1-pyrrolidinecarbodithioato-S,S') vanadium,
(4) insulin aspart (human insulin (28B-L-aspartic acid) or B28-Asp-insulin, also known as insulin X14, INA-X14, NOVORAPID, NOVOMIX, or NOVOLOG);
(5) insulin detemir (Human 29B-(N6-(1-oxotetradecyl)-L-lysine)-(1A-21A), (1B-29B)-Insulin or NN 304);
(6) insulin lispro ("28B-L-lysine-29B-L-proline human insulin, or Lys(B28), Pro(B29) human insulin analog, also known as lys-pro insulin, LY 275585, HUMALOG, HUMALOG MIX 75/25, or HUMALOG MIX 50/50);
(7) insulin glargine (human (A21-glycine, B31-arginine, B32-arginine) insulin HOE 901, also known as LANTUS, OPTISULIN);
(8) Insulin Zinc Suspension, extended (Ultralente), also known as HUMULIN U or ULTRALENTE;
(9) Insulin Zinc suspension (Lente), a 70% crystalline and 30% amorphous insulin suspension, also known as LENTE ILETIN II, HUMULIN L, or NOVOLIN L;

(10) HUMULIN 50/50 (50% isophane insulin and 50% insulin injection);
(11) HUMULIN 70/30 (70% isophane insulin NPH and 30% insulin injection), also known as NOVOLIN 70/30, NOVOLIN 70/30 PenFill, NOVOLIN 70/30 Prefilled;
(12) insulin isophane suspension such as NPH ILETIN II, NOVOLIN N, NOVOLIN N PenFill, NOVOLIN N Prefilled, HUMULIN N;
(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);
(14) ARIAD;
(15) LY 197535;
(16) L-783281; and
(17) TE-17411.

(F) Insulin secretion modulators such as:
(1) glucagon-like peptide-1 (GLP-1) and its mimetics;
(2) glucose-insulinotropic peptide (GIP) and its mimetics;
(3) exendin and its mimetics;
(4) dipeptyl protease (DPP or DPPIV) inhibitors such as
   (4a) DPP-728 or LAF 237 (2-pyrrolidinecarbonitrile,1-(((2-((5-cyano-2-pyridinyl)amino)ethyl)amino)acetyl), known as NVP-DPP-728, DPP-728A, LAF-237);
   (4b) P 3298 or P32/98 (di-(3N-((2S,3S)-2-amino-3-methyl-pentanoyl)-1,3-thiazolidine) fumarate);
   (4c) TSL 225 (tryptophyl-1,2,3,4-tetrahydroisoquinoline-3-carboxylic acid);
   (4d) Valine pyrrolidide (valpyr);
   (4e) 1-aminoalkylisoquinolinone-4-carboxylates and analogues thereof;
   (4f) SDZ 272-070 (1-(L-Valyl)pyrrolidine);
   (4g) TMC-2A, TMC-2B, or TMC-2C;
   (4h) Dipeptide nitriles (2-cyanopyrrolodides);
   (4i) CD26 inhibitors; and
   (4j) SDZ 274-444;
(5) glucagon antagonists such as AY-279955; and
(6) amylin agonists which include, but are not limited to, pramlintide (AC-137, Symlin, tripro-amylin or pramlintide acetate).

(G) Insulin secretagogues, which increase insulin production by stimulating pancreatic beta cells, such as:
(1) asmitiglinide ((2 (S)-cis)-octahydro-gamma-oxo-alpha-(phenylmethyl)-2H-isoindole-2-butanoic acid, calcium salt, also known as mituglimide calcium hydrate, KAD 1229, or S 21403);
(2) Ro 34563;
(3) nateglinide (trans-N-((4-(1-methylethyl)cyclohexyl)carbonyl)-D-phenylalanine, also known as A 4166, AY 4166, YM 026, FOX 988, DJN 608, SDZ DJN608, STARLIX, STARSIS, FASTIC, TRAZEC);
(4) JTT 608 (trans-4-methyl-gamma-oxocyclohexanebutanoic acid);
(5) sulfonylureas such as:
   (5a) chlorpropamide (1-[(p-chlorophenyl)sulfonyl]-3-propylurea, also known as DIABINESE);
   (5b) tolazamide (TOLINASE or TOLANASE);
   (5c) tolbutamide (ORINASE or RASTINON);
   (5d) glyburide (1-[[p-[2-(5-chloro-o-anisamido)ethyl]phenyl]sulfonyl]-3-cyclohexylurea, also known as Glibenclamide, DIABETA, MICRONASE, GLYNASE PresTab, or DAONIL);
   (5e) glipizide (1-cyclohexyl-3-[[p-[2-(5-ethylpyrazinecarboxamido)ethyl]phenyl]sulfonyl]urea, also known as GLUCOTROL, GLUCOTROL XL, MINODIAB, or GLIBENESE);
   (5f) glimepiride (1H-pyrrole-1-carboxamide, 3-ethyl-2, 5-dihydro-4-methyl-N-[2-[4-[[[[(4-methylcyclohexyl)amino]carbonyl]amino]sulfonyl]phenyl]ethyl]-2-oxo-, trans-, also known as Hoe-490 or AMARYL);
   (5g) acetohexamide (DYMELOR);
   (5h) gliclazide (DIAMICRON);
   (5i) glipentide (STATICUM);
   (5j) gliquidone (GLURENORM); and
   (5k) glisolamide (DIABENOR);
(6) $K^+$ channel blockers including, but not limited to, meglitinides such as
   (6a) Repaglinide ((S)-2-ethoxy-4-(2-((3-methyl-1-(2-(1-piperidinyl)phenyl)butyl)amino)-2-oxoethyl)benzoic acid, also known as AGEE 623, AGEE 623 ZW, NN 623, PRANDIN, or NovoNorm);
   (6b) imidazolines; and
   (6c) α-2 adrenoceptor antagonists;
(7) pituitary adenylate cyclase activating polypeptide (PAcAP);
(8) vasoactive intestinal peptide (VIP);
(9) amino acid analogs; and
(10) glucokinase activators.

(H) Growth Factors such as:
(1) insulin-like growth factors (IGF-1, IGF-2);
(2) small molecule neurotrophins;
(3) somatostatin;
(4) growth hormone-releasing peptide (GHRP);
(5) growth hormone-releasing factor (GHRF); and
(6) human growth hormone fragments.

(I) Immunomodulators such as:
(1) vaccines;
(2) T-cell inhibitors
(3) monoclonal antibodies;
(4) interleukin-1 (IL-1) antagonists; and
(5) BDNF.

(J) Other antidiabetic agents:
(1) rHu-Glucagon;
(2) DHEA analogs;
(3) carnitine palmitoyl transferase (CPT) inhibitors;
(4) islet neurogenesis;
(5) pancreatic β amyloid inhibitors; and
(6) UCP (uncoupling protein)-2 and UCP-3 modulators.

In addition, a second RXR modulator, as described above in Section C, may also be utilized as a third antidiabetic agent, provided that it is different from the first RXR modulator.

E. Combinations

The invention features a combination therapy comprising administering a glucose reabsorption inhibitor, such as an SGLT inhibitor, and an RXR modulator for the treatment of diabetes or Syndrome X, or associated symptoms or complications thereof. The demonstrated efficacy of SGLT inhibitors in numerous models of NIDDM validates the utility of this drug alone for the treatment of NIDDM in humans. Since glucose reabsorption inhibitors have a mechanism of action distinct from that of RXR modulators, the disclosed combination with RXR modulators has the advantage of reducing the amount of either drug necessary to achieve combined therapeutic or pharmaceutical efficacy, relative to the use of either drug alone, thereby reducing one or more adverse side-effects, which often include weight gain, edema, cardiac hypertrophy, hepatohypertrophy, hypoglycemia, or hepatotoxicity, or any combination thereof.

The invention provides a method for treating diabetes or Syndrome X, or complications thereof in a subject, said method comprising administering to said subject a jointly effective amount of a glucose reabsorption inhibitor in combination with a jointly effective amount of an RXR modulator. In one aspect of the invention, the RXR modulator is an RXR agonist that increases insulin sensitivity in the subject. In another aspect of the invention, the RXR modulator is an RXR antagonist that increases insulin sensitivity in the subject. Methods to determine the insulin sensitizing activity of an agent are well known in the art. For example, an insulin sensitizer can increase glucose tolerance in a subject in an oral glucose tolerance test.

Particularly, the diabetes or Syndrome X, or associated symptoms or complication thereof is selected from IDDM, NIDDM, IGT, and IFG. More particularly, the RXR modulator is a compound of Formula VI,

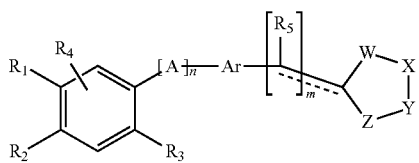

VI wherein $R_1$, R2, R3, R4, R5, A, Ar, m, n, W, X, Y, and Z are as described above in Section C. Preferably, the group

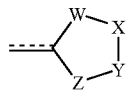

is 2,4-thiazolidinedione

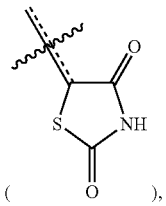

2-thioxo-4-thiazolidinedione

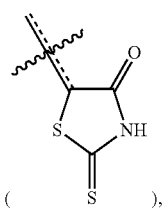

isoxazolidinedione

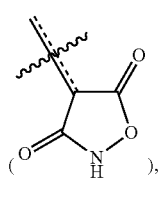

2,4-imidazolidinedione

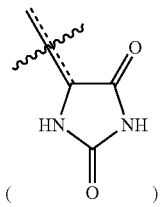

or 2,4-thioxo-4-imidazolidinedione

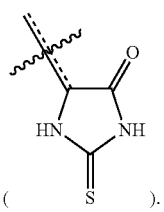

When n is 1, preferably $R_1$ and $R_2$ together with the aromatic ring bonded thereto form a substituted cycloalkyl optionally comprising 1 or 2 heteroatoms selected from O, S, NH or N-alkyl, and $R_3$ is alkyl or substituted alkyl. Also preferably, A is —$CR_6R_7$— wherein $R_6$ and $R_7$ are independently or together alkyl; or $R_6$ and $R_7$ together form a cycloalkyl comprising 1 or 2 oxygen atoms and more preferably a 1,3-dioxolane ring. Still preferably, the group

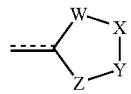

is 2,4-thiazolidinedione, 2-thioxo-4-thiazolidinedione, isoxazolidinedione, 2,4-imidazolidinedione or 2,4-thioxo-4-imidazolidinedione.

Preferably, compounds of Formula VI are selected from:
3-(3,5,5,8,8-pentamethyl-5,6,7,8-tetrahydro-2-naphthyl)-4-trifluoromethoxybenzylidene-2,4-thiazolidinedione;
4-[2-(3,5,5,8,8-pentamethyl-5,6,7,8-tetrahydro-2-naphthyl)-1,3-dioxolane]benzylidene-2,4-thiazolidinedione;
4-[2-(5,5,8,8-tetramethyl-5,6,7,8-tetrahydro-2-naphthyl)-2-propyl]benzylidene-2,4-thiazolidinedione;
4-[2-(3,5,5,8,8-pentamethyl-5,6,7,8-tetrahydro-2-naphthyl)-1,3-dioxolane]benzylidene-2-thioxo-2,4-thiazolidinedione;
4-[2-(5,5,8,8-tetramethyl-5,6,7,8-tetrahydro-2-naphthyl)-2-propyl]benzylidene-2-thioxo-2,4-thiazolidinedione;
4-[2-(3,5,5,8,8-pentamethyl-5,6,7,8-tetrahydro-2-naphthyl)-1,3-dioxolane]benzylidene-2-thioxo-2,4-imidazolidinedione;
4-[2-(5,5,8,8-tetramethyl-5,6,7,8-tetrahydro-2-naphthyl)-2-propyl]benzylidene-2-thioxo-2,4-imidazolidinedione;
4-[2-(3,5,5,8,8-pentamethyl-5,6,7,8-tetrahydro-2-naphthyl)-1,3-dioxolane]benzylidene-2,4-imidazolidinedione;
4-[2-(5,5,8,8-tetramethyl-5,6,7,8-tetrahydro-2-naphthyl)-2-propyl]benzylidene-2,4-imidazolidinedione;
4-[2-(3,5,5,8,8-pentamethyl-5,6,7,8-tetrahydro-2-naphthyl)-1,3-dioxolane]benzyl-2,4-thiazolidinedione;
4-[2-(5,5,8,8-tetramethyl-5,6,7,8-tetrahydro-2-naphthyl)-2-propyl]benzyl-2,4-thiazolidinedione;

4-[2-(3,5,5,8,8-pentamethyl-5,6,7,8-tetrahydro-2-naphthyl)-1,3-dioxolane]benzyl-2-thioxo-2,4-thiazolidinedione;
4-[2-(5,5,8,8-tetramethyl-5,6,7,8-tetrahydro-2-naphthyl)-2-propyl]benzyl-2-thioxo-2,4-thiazolidinedione;
4-[2-(3,5,5,8,8-pentamethyl-5,6,7,8-tetrahydro-2-naphthyl)-1,3-dioxolane]benzyl-2-thioxo-2,4-imidazolidinedione;
4-[2-(5,5,8,8-tetramethyl-5,6,7,8-tetrahydro-2-naphthyl)-2-propyl]benzyl-2-thioxo-2,4-imidazolidinedione;
4-[2-(3,5,5,8,8-pentamethyl-5,6,7,8-tetrahydro-2-naphthyl)-1,3-dioxolane]benzyl-2,4-imidazolidinedione; and
4-[2-(5,5,8,8-tetramethyl-5,6,7,8-tetrahydro-2-naphthyl)-2-propyl]benzyl-2,4-imidazolidinedione.

One of the preferred compounds of Formula VI is MX-6054, which is 2,4-thiazolidinedione, 5-[[3-(5,6,7,8-tetrahydro-3,5,5,8,8-pentamethyl-2-naphthalenyl)-4-(trifluoromethoxy)phenyl]methylene]-, (5Z)-, also named 3-(3,5,5,8,8-pentamethyl-5,6,7,8-tetrahydro-2-naphthyl)-4-trifluoromethoxybenzylidene-2,4-thiazolidinedione, represented by the following formula:

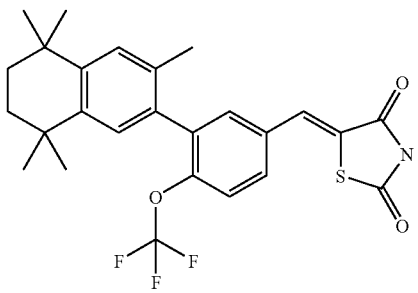

This invention also provides a pharmaceutical composition comprising one or more glucose reabsorption inhibitors, one or more RXR modulators, and a pharmaceutically acceptable carrier. In one aspect of the invention, the RXR modulator is an RXR agonist that increases insulin sensitivity in the subject. In another aspect of the invention, the RXR modulator is an RXR antagonist that increases insulin sensitivity in the subject.

In particular, the glucose reabsorption inhibitor is a SGLT1 and/or SGLT2 inhibitor. More particularly, the glucose reabsorption inhibitor is selected from a propiophenone, a dihydrochalcone, and a derivative thereof.

Specifically, the glucose reabsorption inhibitor is a compound of Formula V:
wherein

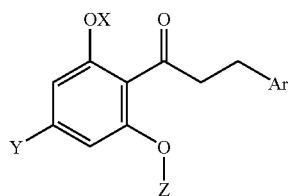

(V)

Ar is aryl or heteroaryl;
OX is an optionally protected hydroxy group;
Y is hydrogen or alkyl; and
Z is glucopyranosyl wherein one or more hydroxy groups thereof may optionally be substituted with one or more groups selected from α-D-glucopyranosyl, alkanoyl, alkoxycarbonyl, and substituted alkyl.
Preferably, Z is β-D-glucopyranosyl.

A preferred group of compounds of Formula V are compounds of Formula I wherein substituents are as described in U.S. Pat. No. 6,048,842, particularly claims 2 through 10.

A preferred group of compounds of Formula V are compounds of Formula II wherein substituents are as described in U.S. Pat. No. 5,830,873, particularly claims 2 through 8 and 13 through 16.

A preferred group of compounds of Formula V are compounds of Formula III wherein substituents are as described in U.S. Pat. No. 5,767,094, particularly claims 2, 3, 8, and 9.

A preferred group of compounds of Formula V are compounds of Formula IV wherein substituents are as described in U.S. Pat. Nos. 5,731,292 and 5,424,406, particularly claims 4 through 13 of U.S. Pat. No. 5,731,292 and claims 6 through 13 and 15 through 18 of U.S. Pat. No. 5,424,406.

Preferably, the glucose reabsorption inhibitor is selected from T-1095 and T-1095A:

T-1095

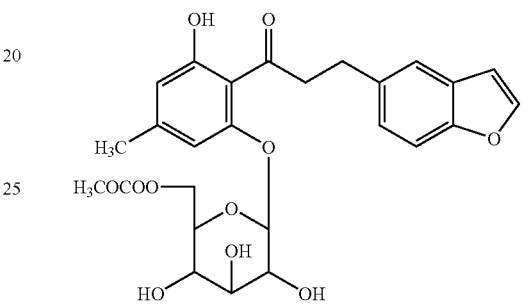

T-1095A

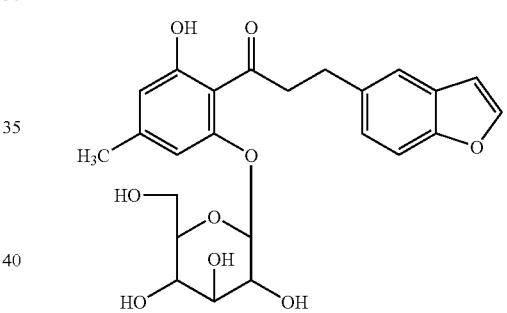

T-1095A is a selective and potent inhibitor of SGLT in the kidney. T-1095 is a pro-drug and converted to its active form T-1095A in the liver. Oral administration of T-1095 has been shown to suppress elevated blood glucose levels by enhancing the excretion of glucose in rodent models of IDDM and NIDDM. Treatment for 3 weeks to 6 months with T-1095 reduced both fed and fasting blood glucose levels and HbA1c in diabetic rodent models (streptozotocin (STZ)-induced diabetic rat, yellow KK mice, db/db mice, Zucker Diabetic Fatty rats and GK rats). In addition, there was a decrease in the hyperinsulinemia, hypertriglyceridemia, and the development of microalbuminuria in the yellow KK mice and other diabetic mice models. The results of oral glucose tolerance test and hyperinsulinemic euglycemic clamp studies revealed the improvement of glucose tolerance and the reduction of insulin resistance. There was no observed sign of adding weight, infection in the urinary tracts, electrolyte imbalance in plasma, changes in food intake, acute hypoglycemic shock nor pathological changes in the kidney during treatment with T-1095. The presence of the carbonate may impart SGLT selectivity. For the intestinal SGLT-1, T-1095A is a better substrate than T-1095. The prodrug is hydrolysed in vivo to yield T-1095A, which is also a better substrate for the inhibition of SGLT-2 in the kidney.

T-1095 or T-1095A may be protected with one or more hydroxyl or diol protecting groups, examples of which are listed above in Section A.

For use in medicine, the salt or salts of the compounds of Formula I, II, III, IV, or V refer to non-toxic "pharmaceutically acceptable salt or salts." Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative basic/cationic salts include, but are not limited to, benzathine, chloroprocaine, choline, diethanolamine, ethylenediamine, meglumine, procaine, aluminum, calcium, lithium, magnesium, potassium, sodium, or zinc. The compounds of Formula I, II, III, IV, or V, or a pharmaceutically acceptable salt thereof, may include an intramolecular salt thereof, or a solvate or hydrate thereof.

F. Administration, Formulation, and Dosages

The utility of the disclosed compounds, compositions, and combinations to treat disorders in glucose and lipid metabolism can be determined according to the procedures well known in the art (see the references listed below), as well as all the procedures described in U.S. Pat. Nos. 5,424,406, 5,731,292, 5,767,094, 5,830,873, and 6,048,842, which are incorporated herein by reference. The compound may be administered to a patient by any conventional route of administration, including, but not limited to, intravenous, oral, subcutaneous, intramuscular, intradermal and parenteral administration. Preferably, formulations are for oral administration.

The present invention also provides pharmaceutical compositions comprising one or more glucose reabsorption inhibitors and one or more RXR modulators in association with a pharmaceutically acceptable carrier.

The daily dosage of the products may be varied over a wide range from 1 to 1000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 or 500 milligrams of the active ingredient for the symptomatic adjustment of the dosage to the patient to be treated. The compounds may be administered on a regimen of 1 to 2 times per day. The dosages, however, may be varied depending upon the requirement of the patients, the severity of the condition being treated and the compound being employed. The use of either daily administration or post-periodic dosing may be employed. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient or ingredients are mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of one or more glucose reabsorption inhibitors and one or more RXR modulators, or a pharmaceutically acceptable salt thereof. When referring to these preformulation compositions as homogeneous, it is meant that the active ingredient or ingredients are dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient or ingredients of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

Advantageously, the combinations of one or more glucose reabsorption inhibitors and one or more RXR modulators of the present invention may be administered in a single daily dose, or the total daily dosage may be administered in divided doses of two, three or four times daily. Furthermore, one or more glucose reabsorption inhibitors and/or one or more RXR modulators according to the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Wherein the present invention is directed to the administration of a combination, the compounds may be co-administered simultaneously, sequentially, or in a single pharmaceutical composition. Where the compounds are administered separately, the number of dosages of each compound given per day, may not necessarily be the same, e.g. where one compound may have a greater duration of activity, and will therefore, be administered less frequently.

Optimal dosages to be administered may be readily determined by those skilled in the art, and will vary with the particular compound used, the strength of the preparation, the mode of administration, and the advancement of the disease condition. In addition, factors associated with the particular patient being treated, including patient age, weight, diet and time of administration, will result in the need to adjust dosages.

The novel compositions of the present invention can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

From Formulae V, VI and other disclosed formulae it is evident that some compounds in the compositions of the invention may have one or more asymmetric carbon atoms in their structure. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereospecific reactions.

Some compounds in the compositions of the present invention may have various individual isomers, such as trans and cis, and various alpha and beta attachments (below and above the plane of the drawing). In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their components enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography. Unless otherwise noted, the scope of the present invention is intended to cover all such isomers or stereoisomers per se, as well as mixtures of cis and trans isomers, mixtures of diastereomers and racemic mixtures of enantiomers (optical isomers) as well.

The therapeutic effect of the glucose reabsorption inhibitor administered in combination with an RXR modulator in treating diabetes, Syndrome X, or associated symptoms or complications can be shown by methods known in the art. The following examples of combination treatment with SGLT inhibitors and RXR agonists are intended to illustrate the invention but not to limit it.

EXAMPLE 1

Effects on Plasma Glucose, Plasma Insulin, Plasma Triglycerides, Plasma Free Fatty Acids, Liver Weight, and Body Weight To examine the effect of T-1095 in combination with an RXR agonist, female db/db mice (6-7 weeks of age/Jackson Labs, ME) are treated daily for 11 days with vehicle (0.5% methylcellulose), an RXR agonist such as MX-6054 (0.1-10 mpk (mg/kg)), T-1095 (100 mpk), or MX-6054 plus T-1095. Mice (n=8 animals/group) receive the test compounds or vehicle by oral gavage in a volume of 10 ml/kg of body weight. Body weight is recorded on day 1, prior to dosing, and days 4, 8 and 11. Eighteen hours after the final dose, mice are weighed and anesthetized with $CO_2/O_2$ (70:30). Mice are then bled by retro-orbital sinus puncture into 2 mL heparinized polypropylene tubes on ice. Plasma samples are then assayed for glucose, insulin, triglycerides, and free fatty acids. Livers are excised, weighed and frozen.

The SGLT inhibitors and RXR agonists have distinct mechanisms of action. Improved glycemic control, measured as a decrease in plasma glucose, plasma insulin, plasma free fatty acids, or plasma triglycerides, or a combination thereof, can be observed at lower concentrations of an RXR agonist such as MX-6054 when given in combination with T-1095. Therefore, a leftward shift in the dose-response curve for effect of an RXR agonist such as MX-6054 on the above parameters can become apparent. In addition, the weight gain observed following treatment with RXR agonists is less pronounced when given with the SGLT inhibitor, since SGLT inhibitors' promotion of the urinary excretion of glucose and loss of calories from the body is demonstrated by reduction in weight or weight gain. Also, since SGLT inhibitors promote a mild diuresis, the edema (and the edematous weight gain) commonly observed after treatment with RXR agonists can be less pronounced or absent. A reduction in the amount of an RXR agonist such as MX-6054 necessary to achieve efficacy in turn improves the side-effect profile. The decreased side effects can include such conditions as fatty liver, increased liver weight, body weight gain, heart weight gain, edema, cardiac hypertrophy, hepatohypertrophy, hypoglycemia, and hepatotoxicity, or any combination thereof.

EXAMPLE 2

Effects on Plasma Glucose, Plasma Insulin, Plasma Free Fatty Acids, Plasma Triglycerides, Liver Weight, and Body Weight To examine the effect of T-1095 in combination with an RXR agonist, female db/db mice (6-7 weeks of age/Jackson Labs, ME) are treated daily for 11 days with vehicle (0.5% methylcellulose), an RXR agonist such as MX-6054 (10 mpk), T-1095 (3, 10, 30, or 100 mpk), or MX-6054 plus T-1095. Mice (n=8 animals/group) receive the test compounds or vehicle by oral gavage in a volume of 10 ml/kg of body weight. Body weight is recorded on day 1, prior to dosing, and days 4, 8 and 11. Eighteen hours after the final dose, mice are weighed and anesthetized with $CO_2/O_2$ (70:30). Mice are then bled by retro-orbital sinus puncture into 2 mL heparinized polypropylene tubes on ice. Plasma samples are then assayed for glucose, insulin, free fatty acids, and triglycerides. Livers are excised, weighed and frozen.

The SGLT inhibitors and RXR agonists have distinct mechanisms of action. The weight gain observed following treatment with RXR agonists is less pronounced when given with the SGLT inhibitor, since SGLT inhibitors' promotion of the urinary excretion of glucose and loss of calories from the body is demonstrated by reduction in weight or weight gain. Also, since SGLT inhibitors promote a mild diuresis, the edema (and the edematous weight gain) commonly observed after treatment with RXR agonists can be less pronounced or absent. A reduction in the amount of RXR agonists necessary to achieve efficacy in turn improves the side-effect profile. The decreased side effects can include such conditions as fatty liver, increased liver weight, body weight gain, increased heart weight/size, edema, cardiac hypertrophy, hepatohypertrophy, hypoglycemia, and hepatotoxicity, or any combination thereof.

EXAMPLE 3

Effects on Plasma Glucose, HbA1c, Hematocrit, Plasma Insulin, Plasma Triglycerides, Plasma Free Fatty Acids, Total Cholesterol, HDL, Plasma Drug Levels, Liver Weight, Heart Weight, Fat Content and Body Weight To examine the effect of T-1095 in combination with an RXR agonist, male ZDF rats (6 weeks of age/GMI) are treated daily for 28 days with vehicle (0.5% methylcellulose), an RXR agonist such as MX-6054 (0.1 mpk-10 mpk), T-1095 (3-100 mpk), or MX-6054 plus T-1095. Rats (n=8 animals/group) receive the test compounds or vehicle by oral gavage in a volume of 2 ml/kg of body weight. Body weight is recorded on day 1, prior to dosing, and twice a week for the duration of the study. On the day prior to the final dose, animals are fasted overnight. One hour after the final dose, rats are weighed and anesthetized with $CO_2/O_2$ (70:30). Rats are then bled by retro-orbital sinus puncture into 2 mL heparinized polypropylene tubes on ice. Rats then receive a glucose challenge (2 g/kg p.o) and are placed in metabolism cages for the urine collection (4 hours). Animals are then sacrificed and epididymal fat pads, livers, and hearts are excised, weighed and frozen for histological examination. Plasma samples are then assayed for glucose, HbA1c, insulin, hematocrit, plasma drug levels, total cholesterol, HDL, free fatty acids, and triglycerides. Urine volume and urinary glucose, protein, osmolarity, electrolytes (Na, K, Cl), BUN, creatinine are measured.

The SGLT inhibitors and RXR agonists have distinct mechanisms of action. Improved glycemic control, measured as a decrease in plasma glucose, HbA1c, plasma insulin, or plasma triglycerides, or a combination thereof, can be observed at lower concentrations of RXR agonists when given in combination with T-1095. Therefore, a leftward shift in the dose-response curve for effect of RXR agonists on the above parameters can become apparent. In addition, the weight gain observed following treatment with RXR agonists is less pronounced when given with the SGLT inhibitor, since SGLT inhibitors' promotion of the urinary excretion of glucose and loss of calories from the body is demonstrated by reduction in weight or weight gain. Also, since SGLT inhibitors promote a mild diuresis, the edema (and the edematous weight gain) commonly observed after treatment with RXR agonists can be less pronounced or absent. This can be demonstrated by a reduction in the RXR agonist-induced increase in heart weight. A reduction in the amount of RXR agonists necessary to achieve efficacy in turn improves the side-effect profile. The decreased side effects can include such conditions as fatty liver, increased liver weight, body weight gain, heart weight gain, edema, cardiac hypertrophy, hepatohypertrophy, hypoglycemia, and hepatotoxicity, or any combination thereof.

EXAMPLE 4

Effects on Plasma Glucose, HbA1c, Hematocrit, Plasma Insulin, Free Fatty Acids, Plasma Triglycerides, Plasma Drug Levels, Liver Weight, Heart Weight, and Body Weight To examine the effect of T-1095 in combination with an RXR agonist, female db/db mice (6 weeks of age/Jackson Labs, ME) are treated daily for 28 days with vehicle (0.5% methylcellulose), an RXR agonist such as MX-6054 (0.1 mpk-10 mpk), T-1095 (3-100 mpk), or MX-6054 plus T-1095. Mice (n=8 animals/group) receive the test compounds or vehicle by oral gavage in a volume of 10 ml/kg of body weight. Body weight is recorded on day 1, prior to dosing, and twice a week for the duration of the study. One hour after the final dose, mice are weighed and anesthetized with $CO_2/O_2$ (70:30). Mice are then bled by retro-orbital sinus puncture into 2 mL heparinized polypropylene tubes on ice. Mice then are then fasted overnight and bled by tail-clip prior to receiving a glucose challenge (2 g/kg p.o). Blood is collected at 30, 60, 120, and 180 minutes after the challenge. Animals are then sacrificed and livers and hearts are excised, weighed and frozen for histological examination. Plasma samples are then assayed for glucose, HbA1c, insulin, hematocrit, drug levels, free fatty acids, and triglycerides.

The SGLT inhibitors and RXR agonists have distinct mechanisms of action. Improved glycemic control, measured as a decrease in plasma glucose, HbA1c, plasma insulin, or plasma triglycerides, or a combination thereof, can be observed at lower concentrations of RXR agonists when given in combination with T-1095. Therefore, a leftward shift in the dose-response curve for effect of RXR agonists on the above parameters can become apparent. In addition, the weight gain observed following treatment with RXR agonists is less pronounced when given with the SGLT inhibitor, since SGLT inhibitors' promotion of the urinary excretion of glucose and loss of calories from the body is demonstrated by reduction in weight or weight gain. Also, since SGLT inhibitors promote a mild diuresis, the edema (and the edematous weight gain) commonly observed after treatment with RXR agonists can be less pronounced or absent. This can be demonstrated by a reduction in the RXR agonist-induced increase in heart weight. A reduction in the amount of RXR agonists necessary to achieve efficacy in turn improves the side-effect profile. The decreased side effects can include such conditions as fatty liver, increased liver weight, body weight gain, heart weight gain, edema, cardiac hypertrophy, hepatohypertrophy, hypoglycemia, and hepatotoxicity, or any combination thereof.

EXAMPLE 5

Effects on Plasma Glucose, Plasma Triglycerides, Liver Weight, Heart Weight and Body Weight To examine the effect of T-1095 in combination with a RXR agonist, male db/db mice (7 weeks of age/Jackson Labs, ME) were treated daily for 11 days with vehicle (0.5% methylcellulose), an RXR agonist such as MX-6054 (0.1 mg/kg-10 mg/kg), T-1095 (100 mg/kg), or MX-6054 plus T-1095. Mice (n=8 animals/group) received the test compounds or vehicle by oral gavage in a volume of 10 ml/kg of body weight. Body weight was recorded on day 1, prior to dosing, and days 4, 8 and 11. Two hours after the final dose (day 11), mice were weighed and anesthetized with $CO_2/O_2$ (70:30). Mice were then bled by retro-orbital sinus puncture into 2 mL heparinized polypropylene tubes on ice. Livers were excised, weighed and frozen.

Plasma samples were then assayed for glucose and triglycerides using Trinder reagent (Sigma Diagnostics) and GPO-Trinder (Sigma Diagnostics). Results are shown in Tables 2 and 3.

TABLE 2

Effect of 11 day oral dosing of MX-6054 +/− T-1095 (100 mg/kg) in 7-8 week old female db/db mice. Effects on fed plasma glucose and triglyceride levels.

| Treatment | Glucose (mg/dL) ± SEM | Triglycerides (mg/dL) ± SEM |
| --- | --- | --- |
| Vehicle Control | 368 ± 68 | 248 ± 35 |
| 0.1 mpk MX-6054 | 357 ± 46 | 260 ± 24 |
| 0.3 mpk MX-6054 | 342 ± 41 | 262 ± 25 |
| 1 mpk MX-6054 | 406 ± 57 | 259 ± 28 |
| 3 mpk MX-6054 | 255 ± 42 | 206 ± 24 |
| 10 mpk MX-6054 | 224 ± 13 * | 189 ± 11 |
| 0.1 mpk MX-6054 + 100 mpk T-1095 | 193 ± 12 ** | 240 ± 24 |
| 0.3 mpk MX-6054 + 100 mpk T-1095 | 228 ± 12 * | 220 ± 38 |
| 1 mpk MX-6054 + 100 mpk T-1095 | 226 ± 21 * | 206 ± 29 |
| 3 mpk MX-6054 + 100 mpk T-1095 | 228 ± 18 | 213 ± 13 |
| 10 mpk MX-6054 + 100 mpk T-1095 | 185 ± 16 ** | 141 ± 8 * |
| 100 mpk T-1095 | 201 ± 9 * | 196 ± 11 |

*p < 0.05 versus the vehicle control.
**p < 0.01 versus the vehicle control.

Livers and hearts were excised, weighed and frozen. Results are shown in Table 3.

TABLE 3

Effect of 35 day oral dosing of MX-6054 +/− T-1095 in 6-7 wks old female db/db mice. Effects on body and liver weights.

| Vehicle Control | −0.7 ± 1.3 | 1.91 ± 0.1 |
| --- | --- | --- |
| 0.1 mpk MX-6054 | −0.7 ± 0.7 | 1.76 ± 0.11 |
| 0.3 mpk MX-6054 | 0.2 ± 0.4 | 1.93 ± 0.09 |
| 1 mpk MX-6054 | 0.6 ± 0.6 | 1.98 ± 0.09 |
| 3 mpk MX-6054 | −0.8 ± 1.3 | 1.89 ± 0.09 |
| 10 mpk MX-6054 | 2.5 ± 1.1 | 2.38 ± 0.16 * |
| 0.1 mpk MX-6054 + 100 mpk T-1095 | −0.8 ± 1.3 | 1.71 ± 0.05 |
| 0.3 mpk MX-6054 + 100 mpk T-1095 | −1.6 ± 0.4 | 1.67 ± 0.05 |
| 1 mpk MX-6054 + 100 mpk T-1095 | −1.0 ± 0.9 | 1.74 ± 0.13 |
| 3 mpk MX-6054 + 100 mpk T-1095 | −0.3 ± 0.9 | 1.89 ± 0.11 |
| 10 mpk MX-6054 + 100 mpk T-1095 | −2.4 ± 0.7 # | 1.99 ± 0.08 # |
| 100 mpk T-1095 | 0.7 ± 0.3 | 1.64 ± 0.07 |

* p < 0.05 versus vehicle,
# p < 0.001 versus the 10 mpk MX-6054 alone,
## p < 0.01 versus 10 mpk MX-6054 alone.

The SGLT inhibitors and RXR agonists have distinct mechanisms of action. Improved glycemic control, measured as a decrease in plasma glucose can be observed at lower concentrations of the RXR agonists when given in combination with T-1095. Specifically, a leftward shift in the dose-response curve for effect of RXR agonists on the plasma glucose was observed.

The above studies show that the oral administration of T-1095 in combination with an RXR modulator improved the status of markers of diabetes mellitus, including blood glucose, and triglyceride levels.

In addition, the weight gain observed following treatment with the highest concentration of the RXR agonists was less pronounced when given with the SGLT inhibitor. This is most likely due to the ability of the SGLT inhibitors to promote the urinary excretion of glucose and loss of calories from the body. Treatment with MX-6054 also produced a significant increase in liver weight which was prevented by the co-administration of T-1095. Therefore, unexpected improvement can be seen in adverse side effects such as increased body weight gain, increased liver weight, fatty liver hepatohypertrophy, hepatotoxicity, and hypoglycemia or any combination thereof.

The above examples can also show that the oral administration of T-1095 in combination with an RXR modulator improve the status of other markers of diabetes mellitus including glycosylated hemoglobin (Hgb A1C) levels. Particularly, the oral administration of T-1095 in combination with one or more RXR modulators can reduce body weight or body weight gain as well as liver weight or liver weight gain, compared to administration of one or more RXR modulators alone.

Thus, for treating diabetes, particularly Type II diabetes mellitus, or Syndrome X, a compound of Formulae I, II, III, IV, or V in combination with one or more RXR modulators, preferably RXR agonists that increases insulin sensitivity, may be employed comprising administering repeated oral doses of the compound of formula I in the range of about 25 to 1000 mg once or twice daily and repeated doses of the anti-diabetic agent or agents at jointly effective dosages. The jointly effective dosage for RXR modulators disclosed herein may be readily determined by those skilled in the art based on standard dosage guidelines. In particular, such combined administration can be effective to accomplish reduction of body weight, body weight gain, liver weight, or liver weight gain in the subject.

Additionally, a method comprising (a) administering to a subject a jointly effective amount of a glucose reabsorption inhibitor; and (b) administering to the subject a jointly effective amount of an RXR modulator can be used to reduce body weight, body weight gain, or liver weight of the subject in need thereof, wherein the combined administration can be in any order and the combined jointly effective amounts provide the desired therapeutic effect.

Also, a method comprising (a) administering to a subject a jointly effective amount of a glucose reabsorption inhibitor; and (b) administering to the subject a jointly effective amount of an RXR modulator can be used to control body weight, body weight gain, liver weight, or liver weight gain of the subject having diabetes, Syndrome X, or associated symptoms or complications, wherein the combined administration can be in any order and the combined jointly effective amounts providing the desired therapeutic effect.

Optimal dosages to be administered may be readily determined by those skilled in the art, and will vary with the particular compound used, the mode of administration, the strength of the preparation and the advancement of the disease condition. In addition, factors associated with the particular patient being treated, including patient's sex, age, weight, diet, time of administration and concomitant diseases, will result in the need to adjust dosages.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

REFERENCES

1. Freychet, P. (1990) Pancreatic Hormones. In Hormones from molecules to disease. Kelly, P. A., Baulieu, E. E., eds., Routledge, Chapman and Hall, New York, N.Y., 491-532.
2. Groop, L. C. (1997) Drug treatment of non-insulin-dependent diabetes mellitus. In Textbook of Diabetes. Pickup, J. C., Williams, G. eds., Blackwell Science, Oxford, UK, 1-18.
3. UK Prospective Diabetes Study Group. (1998) Intensive blood-glucose control with sulfphonylureas or insulin compared with conventional treatment and risk of complications in patients with type 2 diabetes. Lancet 352: 837-853.
4. UK Prospective Diabetes Study Group. (1998) Effect of intensive blood glucose control with metformin on complications in overweight pateints with type 2 diabetes. Lancet 352: 854-865.
5. Conway, B. R. and Demarest, K. T. (2000) Inhibitor of Sodium-Glucose Cotransporter, 1095. Filed Feb. 23, 2000.
6. Evans, A. J., and Krentz, A. J. (1999) Recent developments and emerging therapies for type 2 diabetes mellitus. Drugs R & D 2: 75-94.
7. Day, C. (1999) Thiazolidinediones: a new class of antidiabetic drugs. Diabetic Med. (1999), 16(3), 179-192.
8. Schwartz, S., Raskin, P., Fonseca, V., and Graveline, J. F. (1998) Effect of troglitazone in insulin-treated patients with type 2 diabetes. N. Engl. J. Med. 338: 861-866.
9. Buse, J. B., Gumbiner, B., Mathias, N. P. et al. (1998) Troglitazone use in insulin-treated type 2 diabetic patients. The Troglitazone Insulin study group. Diabetes Care 21: 1455-1461.
10. Mukherjee, R., Davies, P. J. A., Crombie, D. L., Dischoff, E. D., Cesario, R. M. et al. (1997) Sensitization of diabetic and obese mice to insulin by retinoid X receptor agonists. Nature 386: 407-410.
11. Consoli, A. (1992) Diabetes Care 15: 430-441.
12. Gerich, J. E. (1992) Horm. Metab. Res. 26: 18-21.
13. Nestler, J. E., Jakubowicz, D. J., Reamer, P. Et al. (1999) Ovulatory and metabolic effects of D-chiro-inositol in the polycystic ovary syndrome. N. Engl. J. Med. 340: 1314-1320.

What is claimed is:

1. A pharmaceutical composition comprising a glucose reabsorption inhibitor, a RXR modulator, and a pharmaceutically acceptable carrier, wherein the RXR modulator is a compound of Formula (VI),

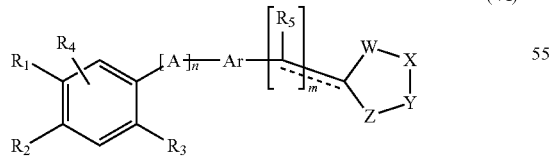

(VI)

or an optical isomer, enantiomer, diastereomer, racemate or racemic mixture thereof, ester, or a pharmaceutically acceptable salt thereof, wherein n and m are independently 0 or 1;

$R_1$ and $R_2$ are 1) independently or together hydrogen, alkyl, substituted alkyl, haloalkyl, alkenyl, substituted alkenyl, alkynyl, substituted alkynyl, alkoxy, substituted alkoxy, hydroxyl, acyl, amino, mono-substituted amino, di-substituted amino, carboxy, carboalkoxy, alkylcarboxamide, substituted alkylcarboxamide, dialkylcarboxamide, substituted dialkylcarboxamide or haloalkoxy; or 2) $R_1$ and $R_2$ together with the aromatic ring bonded thereto form a cycloalkyl, substituted cycloalkyl, cycloalkenyl, substituted cycloalkenyl residue that may optionally comprise 1 or 2 heteroatoms selected from O, S, NH or N-alkyl;

$R_3$ and $R_4$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, thiohaloalkoxy; carboxy, carboalkoxy, alkylcarboxamide, substituted alkylcarboxamide, dialkylcarboxamide, substituted dialkylcarboxamide;

A is —$CR_6R_7$— wherein $R_6$ and $R_7$ are independently or together hydrogen, alkyl, substituted alkyl, alkoxy, substituted alkoxy, haloalkoxy; or $R_6$ and $R_7$ together form a cycloalkyl residue that may optionally comprise 1 or 2 heteroatoms selected from O, S, NH or N-alkyl;

Ar is Formula VII, VIII, IX or X:

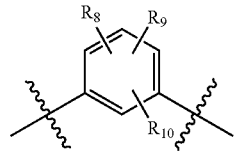

VII

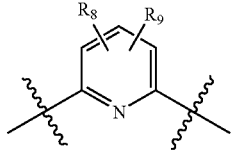

VIII

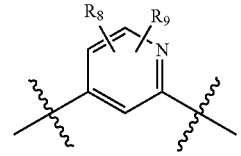

IX

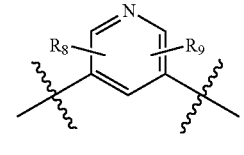

X wherein $R_8$, $R_9$ and $R_{10}$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylamide, alkylsulfonamide, arylsulfonamide, alkylurea, arylurea, alkylcarbamate, arylcarbamate, alkoxy, substituted alkoxy, haloalkoxy, thioalkyl, thiohaloalkoxy; carboxy, carboalkoxy, alkylcarboxamide, substituted alkylcarboxamide, dialkylcarboxamide, substituted dialkylcarboxamide;

R₅ is hydrogen, halogen, hydroxy, alkyl or substituted alkyl;

----- represents a bond present or absent; and

W, X, Y and Z are independently or together —C(O)—, —C(S)—, —S—, —O—, or —NH— residues.

2. The pharmaceutical composition of claim 1, wherein the glucose reabsorption inhibitor is selected from a dihydrochalcone, and a propiophenone, and a derivative thereof.

3. The pharmaceutical composition of claim 2, wherein the glucose reabsorption inhibitor is a compound of Formula (V)

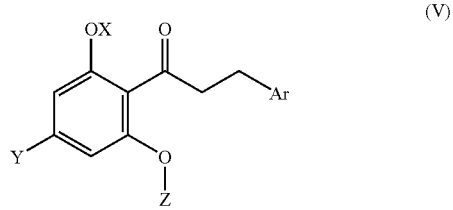

(V)

or an optical isomer, enantiomer, diastereomer, racemate or racemic mixture thereof, ester, or a pharmaceutically acceptable salt thereof, wherein Ar is aryl or heteroaryl;

OX is an optionally protected hydroxy group;

Y is hydrogen or alkyl; and

Z is glucopyranosyl wherein one or more hydroxy groups thereof may optionally be substituted with one or more groups selected from α-D-glucopyranosyl, alkanoyl, alkoxycarbonyl, and substituted alkyl.

4. The pharmaceutical composition of claim 3, wherein the glucose reabsorption inhibitor is a compound of Formula (I)

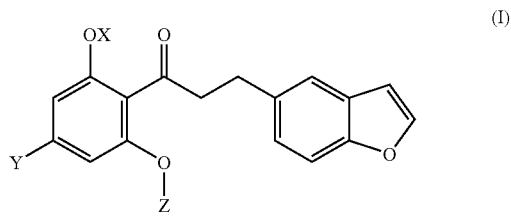

(I)

wherein OX is a hydroxy group which may optionally be protected, Y is a lower alkyl group, and Z is a β-D-glucopyranosyl group wherein one or more hydroxy groups may optionally be protected.

5. The pharmaceutical composition of claim 4, wherein the glucose reabsorption inhibitor is T-1095 or T-1095A, optionally having one or more hydroxyl or diol protecting groups, or an optical isomer, enantiomer, diastereomer, racemate or racemic mixture thereof, ester, or a pharmaceutically acceptable salt thereof.

* * * * *